US008571628B2

(12) United States Patent
Kang et al.

(10) Patent No.: US 8,571,628 B2
(45) Date of Patent: Oct. 29, 2013

(54) APPARATUS AND METHOD FOR HAPTIC RENDERING

(75) Inventors: Hyosig Kang, Weston, FL (US); Arthur E. Quaid, Ft. Lauderdale, FL (US); Dennis Moses, Doral, FL (US)

(73) Assignee: MAKO Surgical Corp., Ft. Lauderdale, FL (US)

(*) Notice: Subject to any disclaimer, the term of this patent is extended or adjusted under 35 U.S.C. 154(b) by 1547 days.

(21) Appl. No.: 11/646,204

(22) Filed: Dec. 27, 2006

(65) Prior Publication Data
US 2007/0142751 A1    Jun. 21, 2007

Related U.S. Application Data

(63) Continuation-in-part of application No. 11/357,197, filed on Feb. 21, 2006, which is a continuation-in-part of application No. 10/384,072, filed on Mar. 6, 2003, and a continuation-in-part of application No. 10/384,077, filed on Mar. 6, 2003, now Pat. No. 7,206,627, and a continuation-in-part of application No. 10/384,194, filed on Mar. 6, 2003, now Pat. No. 7,747,311, said application No. 11/357,197 is a continuation-in-part of application No. 10/621,119, filed on Jul. 16, 2003, now Pat. No. 7,831,292, which is a continuation-in-part of application No. 10/384,078, filed on Mar. 6, 2003.

(60) Provisional application No. 60/362,368, filed on Mar. 6, 2002, provisional application No. 60/655,642, filed on Feb. 22, 2005, provisional application No. 60/759,186, filed on Jan. 17, 2006.

(51) Int. Cl.
*A61B 17/56*    (2006.01)
*A61B 5/05*    (2006.01)

(52) U.S. Cl.
USPC .............. 600/407; 606/53; 606/69; 606/86 R; 901/6; 901/9

(58) Field of Classification Search
None
See application file for complete search history.

(56) References Cited

U.S. PATENT DOCUMENTS

| 4,747,393 A | 5/1988 | Medwid |
| 4,903,536 A | 2/1990 | Salisbury et al. |

(Continued)

FOREIGN PATENT DOCUMENTS

| EP | 1 059 067 A1 | 12/2000 |
| EP | 1 184 684 A2 | 3/2002 |

(Continued)

OTHER PUBLICATIONS

The PCT Search Report dated May 8, 2008 for corresponding PCT Application No. PCT/US2006/049216 (2 pgs.).

(Continued)

*Primary Examiner* — Long V. Le
*Assistant Examiner* — Bradley Impink
(74) *Attorney, Agent, or Firm* — Foley & Lardner LLP

(57) ABSTRACT

In one aspect, the invention relates to a method for generating a haptic penalty force, including in one embodiment, the steps of: defining a primary proxy position; defining a secondary proxy position; defining a HIP position; generating a first force in response to the primary proxy position and the HIP position and generating a second force in response to the secondary proxy position and the HIP position.

17 Claims, 12 Drawing Sheets

(56) References Cited

U.S. PATENT DOCUMENTS

| | | |
|---|---|---|
| 4,979,949 A | 12/1990 | Matsen et al. |
| 5,046,375 A | 9/1991 | Salisbury et al. |
| 5,086,401 A | 2/1992 | Glassman et al. |
| 5,142,930 A | 9/1992 | Allen et al. |
| 5,154,717 A | 10/1992 | Matsen et al. |
| 5,207,114 A | 5/1993 | Salisbury et al. |
| 5,230,338 A | 7/1993 | Allen et al. |
| 5,236,432 A | 8/1993 | Matsen et al. |
| 5,299,288 A | 3/1994 | Glassman et al. |
| 5,343,385 A | 8/1994 | Joskowicz et al. |
| 5,388,480 A | 2/1995 | Townsend |
| 5,399,951 A | 3/1995 | Lavallee et al. |
| 5,408,409 A | 4/1995 | Glassman et al. |
| 5,445,144 A | 8/1995 | Wodicka et al. |
| 5,445,166 A | 8/1995 | Taylor |
| 5,452,941 A | 9/1995 | Halse et al. |
| 5,551,429 A | 9/1996 | Fitzpatrick et al. |
| 5,572,999 A | 11/1996 | Funda et al. |
| 5,576,727 A | 11/1996 | Rosenberg et al. |
| 5,587,937 A * | 12/1996 | Massie et al. ............ 703/7 |
| 5,611,353 A | 3/1997 | Dance et al. |
| 5,625,576 A | 4/1997 | Massie et al. |
| 5,630,431 A | 5/1997 | Taylor |
| 5,638,819 A | 6/1997 | Manwaring et al. |
| 5,676,673 A | 10/1997 | Ferre et al. |
| 5,682,886 A | 11/1997 | Delp et al. |
| 5,688,280 A | 11/1997 | Booth et al. |
| 5,694,013 A | 12/1997 | Stewart et al. |
| 5,695,500 A | 12/1997 | Taylor et al. |
| 5,701,140 A | 12/1997 | Rosenberg et al. |
| 5,704,791 A | 1/1998 | Gillio |
| 5,727,554 A | 3/1998 | Kalend et al. |
| 5,766,016 A | 6/1998 | Sinclair et al. |
| 5,769,640 A | 6/1998 | Jacobus et al. |
| 5,792,147 A | 8/1998 | Evans et al. |
| 5,799,055 A | 8/1998 | Peshkin et al. |
| 5,806,518 A | 9/1998 | Mittelstadt |
| 5,831,408 A | 11/1998 | Jacobus et al. |
| 5,855,553 A | 1/1999 | Tajima et al. |
| 5,871,018 A | 2/1999 | Delp et al. |
| 5,887,121 A | 3/1999 | Funda et al. |
| 5,888,220 A | 3/1999 | Felt et al. |
| 5,898,599 A | 4/1999 | Massie et al. |
| 5,928,137 A | 7/1999 | Green |
| 5,950,629 A | 9/1999 | Taylor et al. |
| 5,976,156 A | 11/1999 | Taylor et al. |
| 5,978,696 A | 11/1999 | VomLehn et al. |
| 5,980,535 A | 11/1999 | Barnett et al. |
| 5,984,930 A | 11/1999 | Maciunas et al. |
| 5,987,960 A | 11/1999 | Messner et al. |
| 6,002,859 A | 12/1999 | DiGioia, III et al. |
| 6,006,126 A | 12/1999 | Cosman |
| 6,006,127 A | 12/1999 | Van Der Brug et al. |
| 6,017,305 A | 1/2000 | Bonutti |
| 6,033,415 A | 3/2000 | Mittelstadt et al. |
| 6,084,587 A | 7/2000 | Tarr et al. |
| 6,104,158 A | 8/2000 | Jacobus et al. |
| 6,109,270 A | 8/2000 | Mah et al. |
| 6,111,577 A * | 8/2000 | Zilles et al. .............. 715/701 |
| 6,113,395 A | 9/2000 | Hon |
| 6,147,674 A | 11/2000 | Rosenberg et al. |
| 6,161,032 A | 12/2000 | Acker |
| 6,188,728 B1 | 2/2001 | Hurst |
| 6,191,796 B1 | 2/2001 | Tarr |
| 6,205,411 B1 | 3/2001 | DiGioia, III et al. |
| 6,219,032 B1 | 4/2001 | Rosenberg et al. |
| 6,223,100 B1 | 4/2001 | Green |
| 6,226,566 B1 | 5/2001 | Funda et al. |
| 6,228,089 B1 | 5/2001 | Wahrburg |
| 6,231,526 B1 | 5/2001 | Taylor et al. |
| 6,233,504 B1 | 5/2001 | Das et al. |
| 6,259,806 B1 | 7/2001 | Green |
| 6,285,902 B1 | 9/2001 | Kienzle et al. |
| 6,288,705 B1 | 9/2001 | Rosenberg et al. |
| 6,292,174 B1 | 9/2001 | Mallett et al. |
| 6,300,936 B1 | 10/2001 | Braun et al. |
| 6,322,467 B1 | 11/2001 | Hook et al. |
| 6,322,567 B1 | 11/2001 | Mittelstadt et al. |
| 6,325,808 B1 | 12/2001 | Bernard et al. |
| 6,337,994 B1 | 1/2002 | Stoianovici et al. |
| 6,366,273 B1 | 4/2002 | Rosenberg et al. |
| 6,369,834 B1 | 4/2002 | Zilles et al. |
| 6,377,011 B1 | 4/2002 | Ben-Ur |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,393,340 B2 | 5/2002 | Funda et al. |
| 6,405,072 B1 | 6/2002 | Cosman |
| 6,405,158 B1 | 6/2002 | Massie et al. |
| 6,417,638 B1 | 7/2002 | Guy et al. |
| 6,421,048 B1 | 7/2002 | Shih et al. |
| 6,424,885 B1 | 7/2002 | Niemeyer et al. |
| 6,430,434 B1 | 8/2002 | Mittelstadt |
| 6,434,416 B1 | 8/2002 | Mizoguchi et al. |
| 6,443,894 B1 | 9/2002 | Sumanaweera et al. |
| 6,466,815 B1 | 10/2002 | Saito et al. |
| 6,468,265 B1 | 10/2002 | Evans et al. |
| 6,493,608 B1 | 12/2002 | Niemeyer |
| 6,494,039 B2 | 12/2002 | Pratt et al. |
| 6,533,737 B1 | 3/2003 | Brosseau et al. |
| 6,546,277 B1 | 4/2003 | Franck et al. |
| 6,547,782 B1 | 4/2003 | Taylor |
| 6,551,325 B2 | 4/2003 | Neubauer et al. |
| 6,552,722 B1 | 4/2003 | Shih et al. |
| 6,583,161 B1 | 6/2003 | Medina |
| 6,642,686 B1 | 11/2003 | Ruch |
| 6,671,651 B2 | 12/2003 | Goodwin et al. |
| 6,674,916 B1 | 1/2004 | Deman et al. |
| 6,690,964 B2 | 2/2004 | Bieger et al. |
| 6,692,485 B1 | 2/2004 | Brock et al. |
| 6,701,174 B1 | 3/2004 | Krause et al. |
| 6,704,694 B1 | 3/2004 | Basdogan et al. |
| 6,711,431 B2 | 3/2004 | Sarin et al. |
| 6,711,432 B1 | 3/2004 | Krause et al. |
| 6,748,819 B2 | 6/2004 | Maeguchi et al. |
| 6,750,877 B2 | 6/2004 | Rosenberg et al. |
| 6,757,582 B2 | 6/2004 | Brisson et al. |
| 6,778,850 B1 | 8/2004 | Adler et al. |
| 6,785,572 B2 | 8/2004 | Yanof et al. |
| 6,786,896 B1 | 9/2004 | Madhani et al. |
| 6,801,801 B1 | 10/2004 | Sati |
| 6,810,281 B2 | 10/2004 | Brock et al. |
| 6,816,148 B2 | 11/2004 | Mallett et al. |
| 6,831,640 B2 | 12/2004 | Shih et al. |
| 6,850,794 B2 | 2/2005 | Shahidi |
| 6,853,965 B2 | 2/2005 | Massie et al. |
| 6,859,661 B2 | 2/2005 | Tuke |
| 6,877,239 B2 | 4/2005 | Leitner et al. |
| 6,894,678 B2 | 5/2005 | Rosenberg et al. |
| 6,920,347 B2 | 7/2005 | Simon et al. |
| 6,985,133 B1 | 1/2006 | Rodomista et al. |
| 6,987,504 B2 | 1/2006 | Rosenberg et al. |
| 7,001,346 B2 | 2/2006 | White |
| 7,035,716 B2 | 4/2006 | Harris et al. |
| 7,039,866 B1 | 5/2006 | Rosenberg et al. |
| 7,131,073 B2 | 10/2006 | Rosenberg et al. |
| 7,168,042 B2 | 1/2007 | Braun et al. |
| 7,199,790 B2 | 4/2007 | Rosenberg et al. |
| 7,206,626 B2 | 4/2007 | Quaid, III |
| 7,206,627 B2 | 4/2007 | Abovitz et al. |
| 7,491,198 B2 | 2/2009 | Kockro et al. |
| 7,660,623 B2 | 2/2010 | Hunter et al. |
| 7,742,804 B2 | 6/2010 | Faul |
| 7,747,311 B2 | 6/2010 | Quaid, III |
| 7,774,044 B2 | 8/2010 | Sauer et al. |
| 7,831,292 B2 | 11/2010 | Quaid et al. |
| 2001/0034530 A1 | 10/2001 | Malackowski et al. |
| 2001/0037064 A1 | 11/2001 | Shahidi |
| 2001/0039422 A1 | 11/2001 | Carol et al. |
| 2001/0041838 A1 | 11/2001 | Holupka et al. |
| 2002/0082498 A1 | 6/2002 | Wendt et al. |
| 2002/0107521 A1 | 8/2002 | Petersen et al. |
| 2002/0108054 A1 | 8/2002 | Moore et al. |
| 2002/0120188 A1 | 8/2002 | Brock et al. |

(56) References Cited

U.S. PATENT DOCUMENTS

| | | |
|---|---|---|
| 2002/0133174 A1 | 9/2002 | Charles et al. |
| 2003/0112281 A1 | 6/2003 | Sriram et al. |
| 2003/0209096 A1 | 11/2003 | Pandey et al. |
| 2004/0012806 A1 | 1/2004 | Murata |
| 2004/0024311 A1 | 2/2004 | Quaid, III |
| 2004/0034282 A1 | 2/2004 | Quaid et al. |
| 2004/0034283 A1 | 2/2004 | Quaid |
| 2004/0034302 A1 | 2/2004 | Abovitz et al. |
| 2004/0102866 A1 | 5/2004 | Harris et al. |
| 2004/0106916 A1 | 6/2004 | Quaid et al. |
| 2004/0115606 A1 | 6/2004 | Davies |
| 2004/0127788 A1 | 7/2004 | Arata |
| 2004/0128026 A1 | 7/2004 | Harris et al. |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0013477 A1 | 1/2005 | Ratti et al. |
| 2005/0062738 A1 | 3/2005 | Handley et al. |
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0137599 A1 | 6/2005 | Masini |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0215879 A1 | 9/2005 | Chuanggui |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0109266 A1* | 5/2006 | Itkowitz et al. .............. 345/419 |
| 2006/0133827 A1 | 6/2006 | Becouarn et al. |
| 2006/0142657 A1 | 6/2006 | Quaid et al. |
| 2006/0293598 A1 | 12/2006 | Fraser |
| 2007/0260140 A1 | 11/2007 | Solar et al. |
| 2007/0270685 A1 | 11/2007 | Kang et al. |
| 2008/0004633 A1 | 1/2008 | Arata et al. |
| 2008/0010705 A1 | 1/2008 | Quaid et al. |
| 2008/0010706 A1 | 1/2008 | Moses et al. |
| 2008/0058945 A1 | 3/2008 | Hajaj et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |

FOREIGN PATENT DOCUMENTS

| | | |
|---|---|---|
| EP | 1 380 266 A1 | 1/2004 |
| EP | 1 574 186 | 6/2008 |
| JP | 8-215211 | 8/1996 |
| JP | 09-330016 A | 12/1997 |
| JP | 2000-279425 | 10/2000 |
| JP | 2002-102251 | 4/2002 |
| JP | 2003-053684 | 2/2003 |
| JP | 2004-513684 | 5/2004 |
| WO | WO-95/01757 A1 | 1/1995 |
| WO | WO-96/17552 A1 | 6/1996 |
| WO | WO-00/35336 A2 | 6/2000 |
| WO | WO 02/24051 | 3/2002 |
| WO | WO-02/060653 A2 | 8/2002 |
| WO | WO-02/061371 A1 | 8/2002 |
| WO | WO 02/061688 | 8/2002 |
| WO | WO 03/077101 A2 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO-2004/070577 A1 | 8/2004 |
| WO | WO-2004/070580 A2 | 8/2004 |
| WO | WO-2004/070581 A2 | 8/2004 |
| WO | WO-2004-075987 A1 | 9/2004 |
| WO | WO-2005/009215 A | 2/2005 |
| WO | WO 2005-072629 | 8/2005 |
| WO | WO-2005/120380 A1 | 12/2005 |
| WO | WO-2005/122916 A1 | 12/2005 |
| WO | WO 2006/004894 A2 | 1/2006 |
| WO | WO-2006/091494 A1 | 8/2006 |
| WO | WO-2007/117297 A2 | 10/2007 |

OTHER PUBLICATIONS

Abovitz et al., "The Future Use of Networked Haptic Learning Information Systems in Computer-Assisted Surgery," CAOS 2001, Jul. 6-8, 2001, pp. 337-338.

Abovitz, "Digital surgery: the future of medicine and human-robot symbiotic interaction," Industrial Robot: An International Journal, Oct. 2001, vol. 28, Issue 5, pp. 401-406 (abstract only).

Abovitz, "Human-Interactive Medical Robotics," CAOS 2000, Jun. 15-17, 2000, pp. 71-72.

Abovitz, "Human-Interactive Medical Robotics," CAOS 2001, Jul. 6-8, 2001, pp. 81-82.

Bennett et al., "Autonomous Calibration of Single-Loop Kinematic Chains Formed by Manipulators With Passive End-Point Constraints," IEEE Transactions Closed on Robotics and Automation, vol. 7 (5), pp. 597-606, 1991.

Bettini et al., "Vision assisted control for manipulation using virtual fixtures: Experiments at macro and micro scales," in Proc. 2002 IEEE Intl. Conf. on Robotics and Automation, (Washington, DC), May 2002.

Cobb et al., "A robotic system for TKR surgery," in Third Annual North American Program on Computer Assisted Orthopaedic Surgery, (Pittsburgh, PA), pp. 71-74, Jun. 1999.

Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.

Goswami, et al., "Identifying Robot Parameters Using Partial Pose Information," IEEE Control Systems Magazine, Oct. 1993.

Hollerbach, J.M. & D. E. Johnson. Virtual Environment Rendering. To appear in Human and Machine Haptics, M. Cutkosky, R. Howe, K. Salisbury, and M. Srinivasan (eds.), MIT Press, 2000 (available at http://www.cs.ubc.ca/labs/spin/publications/related/hollerbach00.pdf).

Kanazides, Peter et al., "An Integrated System for Cementless Hip Replacement", Integrated Surgical Systems Department of Orthopedic Surgery, Sutter General Hospital, May/Jun. 1995, pp. 307-313.

Leeser et al., "Computerassisted teach and play: Novel user-friendly robot teach mode using gravity compensation and backdrivability," in Proceedings of the Robotics International/SME Fifth World Conference on Robotics Research, (Cambridge, MA), Sep. 1994.

Meggiolaro, et al., "Manipulator calibration using a single endpoint contact constraint," in 26th ASME Bienniel Mechanisms Conference, (Baltimore, MD), 2000.

Park et al., "Virtual fixtures for robotic cardiac surgery," in Proc. Medical Image Computing and Computer-Assisted Intervention, (Utrecht, Netherlands), Oct 2001.

Quaid et al., "Haptic Information Displays for Computer-Assisted Surgery," Proceedings of the 2002 IEEE International Conference on Robotics & Automation, May 2002, pp. 2092-2097.

Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.

Roche, "Changing the way surgeons plan and execute minimally invasive unicompartmental knee surgery," Orthopaedic Product News, pp. 16-18, Jul./Aug. 2006.

Rosenberg, Virtual Fixtures: Perceptual overlays enhance operator performance in telepresence tasks. PhD thesis, Stanford University, Aug. 1994.

Taylor, Russell et al., "An Image-Directed Robotic System for Precise Orthopaedic Surgery", IEEE Transactions on Robotics and Automation, vol. 10, No. 3, Jun. 1994, pp. 261-275.

(56) References Cited

OTHER PUBLICATIONS

Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.
Taylor, Russell et al., "Robotic Joint Replacement Surgery", NSF Engineering Research Center for Computer-Integrated Surgical Systems and Technology, 2000, 2001, 2004.
Townsend et al., "Teleoperator slave—WAM design methodology," Industrial Robot, vol. 26, No. 3, pp. 167-177, 1999.
U.S. Appl. No. 11/750,807, filed May 18, 2007, Arata et al.
U.S. Appl. No. 11/750,815, filed May 18, 2007, Kang et al.
U.S. Appl. No. 11/750,840, filed May 18, 2007, Quaid et al.
U.S. Appl. No. 11/750,845, filed May 18, 2007, Moses et al.
Advisory Action for U.S. Appl. No. 11/750,815, mail date Feb. 22, 2011, 3 pages.
Applicant's response to Office Action for U.S. Appl. No. 11/750,815, submitted Feb. 10, 2011, 12 pages.
Applicant's response to Office Action for U.S. Appl. No. 11/750,815, submitted Mar. 31, 2010, 18 pages.
Applicant's response to Office Action for U.S. Appl. No. 11/750,815, submitted Nov. 23, 2009, 2 pages.
Applicant's response to Office Action for U.S. Appl. No. 11/750,815, submitted Sep. 13, 2010, 12 pages.
Applicant's response to Office Action for U.S. Appl. No. 11/750,840, submitted May 16, 2011, 11 pages.
Applicant's response to Office Action for U.S. Appl. No. 11/750,840, submitted Oct. 21, 2010, 5 pages.
Examination report for EP 04757075.9, dated Jan. 12, 2011.
Examiner Interview Summary Record for U.S. Appl. No. 11/750,815, mail date Sep. 14, 2010, 3 pages.
Office Action and English translation for Chinese Application No. 200780018181.9, dated Jun. 10, 2010 (10 pages).
Office Action for U.S. Appl. No. 11/750,815, mail date Dec. 31, 2009, 11 pages.
Office Action for U.S. Appl. No. 11/750,815, mail date Jun. 11, 2010, 10 pages.
Office Action for U.S. Appl. No. 11/750,815, mail date Nov. 4, 2010, 11 pages.
Office Action for U.S. Appl. No. 11/750,815, mail date Oct. 27, 2009, 7 pages.
Office Action for U.S. Appl. No. 11/750,840, mail date Jul. 23, 2010, 17 pages.
Office Action for U.S. Appl. No. 11/750,840, mail date Nov. 16, 2010, 10 pages.
Office Action with English translation for Japanese Application No. 2008-551271, dated May 18, 2011 (6 pages).
Ho, S. C., et al., "Robot Assisted Knee Surgery Establishing a Force Control Strategy Incorporating Active Motion Constraint", IEEE Engineering in Medicine and Biology Magazine, IEEE Service Center, vol. 14, No. 3, pp. 292-300 (1995) XP0005085, ISSN: 0739-5175, p. 293.
PCT/US2006/049216, Partial Intl. Search Report, Jan. 18, 2008 (2 pgs.).
U.S. Appl. No. 10/384,072, filed Mar. 6, 2003, Quaid et al.
U.S. Appl. No. 10/384,077, filed Mar. 6, 2003, Abovitz et al.
U.S. Appl. No. 10/384,078, filed Mar. 6, 2003, Quaid et al.
U.S. Appl. No. 10/384,194, filed Mar. 6, 2003, Quaid et al.
U.S. Appl. No. 10/621,119, filed Jul. 16, 2003, Quaid et al.
U.S. Appl. No. 11/357,197, filed Feb. 21, 2006, Quaid et al.
U.S. Appl. No. 12/144,496, filed Jun. 23, 2008, Quaid et al.
U.S. Appl. No. 12/144,507, filed Jun. 23, 2008, Quaid et al.
U.S. Appl. No. 12/144,517, filed Jun. 23, 2008, Quaid et al.
U.S. Appl. No. 12/144,526, filed Jun. 23, 2008, Quaid et al.
U.S. Appl. No. 12/698,353, filed Feb. 2, 2010, Quaid et al.
Applicant's response to Final Office Action for U.S. Appl. No. 12/144,526, submitted Mar. 15, 2011.
Applicant's response to non-final Office Action for U.S. Appl. No. 12/144,507, submitted Sep. 15, 2010.
Applicant's response to non-final Office Action for U.S. Appl. No. 12/144,517, submitted Sep. 8, 2010.
Applicant's response to non-final Office Action for U.S. Appl. No. 12/144,526, submitted Jul. 29, 2010.
Applicant's response to $1^{st}$ Office Action for Chinese Application No. 200680012488.3, submitted May 14, 2010 (10 pages).
Applicant's response to $2^{nd}$ Office Action for Chinese Application No. 200680012488.3, submitted Dec. 7, 2010 (3 pages).
Chapter II Demand and Response to Written Opinion for PCT/US2006/005700, submitted Dec. 15, 2006 (16 pages).
Chapter II Demand and Response to Written Opinion for PCT/US2006/049216, submitted Jul. 15, 2008.
English translation of first Office Action for related Chinese Application No. 200680012488.3, dated Jan. 15, 2010 (6 pages).
International Preliminary Report on Patentability for PCT/US2006/005700, dated May 8, 2007 (7 pages).
International Preliminary Report on Patentability for PCT/US2006/049216, dated Sep. 10, 2008.
Written Opinion for PCT/US2006/049216, dated May 8, 2008.
International Search Report and Written Opinion for PCT/US2006/005700, dated Jun. 27, 2006.
Notice of Appeal and Pre-Appeal Brief Request for Review filed in response to Final Office Action for U.S. Appl. No. 12/144,507, submitted Mar. 22, 2011.
Notice of Appeal and Pre-Appeal Brief Request for Review filed in Response to Final Office Action for U.S. Appl. No. 12/144,517, submitted Mar. 22, 2011.
Office Action for U.S. Appl. No. 12/144,507, mail date Jun. 17, 2010, 7 pages.
Office Action for U.S. Appl. No. 12/144,507, mail date Nov. 22, 2010, 9 pages.
Office Action for U.S. Appl. No. 12/144,517, mail date Jun. 9, 2010, 7 pages.
Office Action for U.S. Appl. No. 12/144,517, mail dated Nov. 22, 2010, 8 pages.
Office Action for U.S. Appl. No. 12/144,526, mail date Apr. 29, 2010, 9 pages.
Office Action for U.S. Appl. No. 12/144,526, mail date Nov. 15, 2010, 11 pages.
Second Office Action and English translation for related Chinese Application No. 200680012488.3, dated Oct. 12, 2010 (10 pages).
Office Action for U.S. Appl. No. 10/384,072, mail date May 18, 2006, 6 pages.
Applicant's response to Office Action for U.S. Appl. No. 10/384,072, submitted Aug. 21, 2006, 14 pages.
Notice of Allowance for U.S. Appl. No. 10/384,072, mail date Dec. 21, 2006, 7 pages.
Office Action for U.S. Appl. No. 10/384,077, mail date Jun. 1, 2006, 8 pages.
Applicant's response to Office Action for U.S. Appl. No. 10/384,077, submitted Aug. 21, 2006, 22 pages.
Notice of Allowance for U.S. Appl. No. 10/384,077, mail date Dec. 14, 2006, 8 pages.
Office Action for U.S. Appl. No. 10/384,078, mail date Feb. 4, 2008, 9 pages.
Applicant's response to Office Action for U.S. Appl. No. 10/384,078, submitted Apr. 25, 2008, 10 pages.
Office Action for U.S. Appl. No. 10/384,078, mail date Oct. 7, 2008, 8 pages.
Applicant's response to Office Action for U.S. Appl. No. 10/384,078, submitted Jan. 7, 2009, 12 pages.
Office Action for U.S. Appl. No. 10/384,078, mail date Apr. 9, 2009, 13 pages.
Applicant's response to Office Action for U.S. Appl. No. 10/384,078, submitted Jul. 8, 2009, 17 pages.
Office Action for U.S. Appl. No. 10/384,078, mail date Nov. 25, 2009, 14 pages.
Applicant's response to Office Action for U.S. Appl. No. 10/384,078, submitted Feb. 15, 2010, 14 pages.
Applicant's Pre-Appeal Brief Conference Request for U.S. Appl. 10/384,078, submitted Feb. 25, 2010, 5 pages.
Advisory Action for U.S. Appl. No. 10/384,078, mail date Mar. 1, 2010, 3 pages.

(56) References Cited

OTHER PUBLICATIONS

Pre-Appeal Conference Decision for U.S. Appl. No. 10/384,078, mail date Mar. 15, 2010, 2 pages.
Appeal Brief for U.S. Appl. No. 10/384,078, submitted Apr. 22, 2010, 42 pages.
Office Action for U.S. Appl. No. 10/384,078, mail date Jul. 20, 2010, 12 pages.
Examiner Interview Summary Record for U.S. Appl. No. 10/384,078, mail date Oct. 15, 2010, 3 pages.
Applicant's response to Office Action for U.S. Appl. No. 10/384,078, submitted Oct. 19, 2010, 16 pages.
Office Action for U.S. Appl. No. 10/384,078, mail date Dec. 30, 2010, 21 pages.
Applicant's response to Office Action for U.S. Appl. No. 10/384,078, submitted Mar. 29, 2011, 16 pages.
Terminal Disclaimer for U.S. Appl. No. 10/384,078, submitted Mar. 30, 2011, 1 pages.
Terminal Disclaimer Review Decision for U.S. Appl. No. 10/384,078, mailed Apr. 14, 2011, 1 page.
Office Action for U.S. Appl. No. 10/384,194, mail date Jun. 18, 2008, 2010, 9 pages.
Applicant's response to Office Action for U.S. Appl. No. 10/384,194, submitted Nov. 18, 2008, 19 pages.
Office Action for U.S. Appl. No. 10/384,194, mail date Mar. 2, 2009, 2010, 11 pages.
Applicant's response to Office Action for U.S. Appl. No. 10/384,194, submitted May 1, 2009, 20 pages.
Advisory Action for U.S. Appl. No. 10/384,194, mail date May 22, 2009, 3 pages.
Applicant's response to Office Action for U.S. Appl. No. 10/384,194, submitted Jun. 1, 2009, 20 pages.
Office Action for U.S. Appl. No. 10/384,194, mail date Nov. 2, 2009, 8 pages
Applicant's response to Office Action for U.S. Appl. No. 10/384,194, submitted Feb. 2, 2010, 13 pages.
Notice of Allowance for U.S. Appl. No. 10/384,194, mail date Apr. 15, 2010, 4 pages.
Office Action for U.S. Appl. No. 10/621,119, mail date Jun. 16, 2006, 6 pages.
Applicant's response to Office Action for U.S. Appl. No. 10/621,119, submitted Sep. 14, 2006, 23 pages.
Notice of Non-Compliant or Non-Responsive Amendment for U.S. Appl. No. 10/621,119, mail date Sep. 20, 2006, 2 pages.
Applicant's response to Office Action for U.S. Appl. No. 10/621,119, submitted Oct. 2, 2006, 25 pages.
Office Action for U.S. Appl. No. 10/621,119, mail date Sep. 4, 2007, 8 pages.
Applicant's response to Office Action for U.S. Appl. No. 10/621,119, submitted Dec. 4, 2007, 19 pages.
Office Action for U.S. Appl. No. 10/621,119, mail date Jun. 9, 2008, 9 pages.
Applicant's response to Office Action for U.S. Appl. No. 10/621,119, submitted Aug. 8, 2008, 24 pages.
Advisory Action for U.S. Appl. No. 10/621,119, mail dated Sep. 17, 2008, 3 pages.
Pre-Appeal Brief Conference Request for U.S. Appl. No. 10/621,119, submitted Oct. 9, 2008, 6 pages.
Office Action for U.S. Appl. No. 10/621,119, mail date Dec. 10, 2008, 10 pages.
Applicant's response to Office Action for U.S. Appl. No. 10/621,119, submitted Mar. 9, 2009, 20 pages.
Office Action for U.S. Appl. No. 10/621,119, mail date Sep. 29, 2009, 9 pages.
Applicant's response to Office Action for U.S. Appl. No. 10/621,119, submitted Nov. 13, 2009, 19 pages.
Office Action for U.S. Appl. No. 10/621,119, mail date Feb. 3, 2010, 12 pages.
Applicant's response to Office Action for U.S. Appl. No. 10/621,119, submitted Apr. 30, 2010, 19 pages.
Notice of Allowance and Examiner Interview Summary Record for U.S. Appl. No. 10/621,119, mail date Jun. 11, 2010, 9 pages.
Acosta, et al., "Development of a Haptic Virtual Environment", Computer-Based Medical Systems, Proceedings 12th IEEE Symposium. pp. 35-39, 1999.
Bettini, A., et al., "Vision Assisted Control for Manipulation Using Virtual Fixtures," proceedings of the 2001 Institute of Electrical and Electronics Engineers International Conference on Intelligent Robots and Systems, Oct. 29-Nov. 3, 2001, pp. 1171-1176
Colgate, J. Edward, et al., "Cobots: Robots for Collaboration with Human Operators," proceedings of International Mechanical Engineering Congress & Exhibition, DSC-vol. 58, 1996, pp. 433-439.
Chen et al., "Force Feedback for Surgical Simulation," Proceedings of the IEEE, New York, US, vol. 86, No. 3, Mar. 1, 1998. pp. 524-530.
Davies et al, "Acrobot-using Robots and Surgeons Synergistically in Knee Surgery", 1997 British Crown Copyright, 173-178.
Fritz, et al., "Design of a Haptic Data Visualization System for People with Visual Impairments", IEEE Trans. on Rehabiliation Engineering, vol. 7, No. 3, Sep. 1999.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "'Acrobot' capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Moore, Carl A., et al., "Cobot Implementation of 3D Virtual Surfaces," proceedings of the 2002 Institute of Electrical and Electronics Engineers International Conference on Robotics & Automation, May 2002, pp. 3242-3247.
Niki, et al., "Simple Haptic Display and Object Data Design", Proceedings of the 2000 IEEE/RSJ International Conference on Intelligent Robots and Systems, pp. 967-972, 2000.
Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Press Release, "The Acrobot Company Wins Best Surgical Innovation Award," Acrobot Precision Surgical Systems, May 24, 2002, 1 page.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Rosenberg, "Virtual Fixtures: Perceptual Tools for Telerobotic Manipulation", 1993 IEEE, 76-82.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider, O., et al., "Synergistic Robotic Assistance to Cardiac Procedures," presented to Computer Assisted Radiology and Surgery on Jun. 23-26, 1999, 5 pages.
Sensable Technologies, Inc., "Freeform Feel the Difference", 2001, 4 pages.
Sensable Technologies, Inc., "FreeForm Modeling—Technical Features," 2003, 2 pages.
Tognetti, Lawrence Joseph, "Actuator Design for a Passive Haptic Display," Georgia Institute of Technology, Jun. 1999, 33 pages.
World Wide Web, http://www.acrobot.co.uk/home.html, "The Acrobot Company Limited—Precision Surgical Systems," printed on Jul. 10, 2002, 1 page.
World Wide Web, http://www.acrobot.co.uk/background.html, "The Acrobot Company Limited—Background," printed on Jul. 10, 2002, 1 page.
World Wide Web, http://www.acrobot.co.uk/products.html, "The Acrobot Company Limited—Products," printed on Jul. 10, 2002, pp. 1-6.

(56) References Cited

OTHER PUBLICATIONS

World Wide Web, http://www.acrobot.co.uk/meetings.html, "The Acrobot Company Limited—Meetings and Publications," printed on Jul. 10, 2002, pp. 1-3.
World Wide Web, http://www.fcs-cs.com/robotics/content/hapticmaster.htm, "HapticMASTER", printed on Jun. 12, 2003, 1 page.
World Wide Web, http://www.fcs-cs.com/robotics/content/endeffectors.htm, "End effectors," printed on Jun. 12, 2003, 1 page.
World Wide Web, http://www.fcs-cs.com/robotics/content/software.htm, "Software," printed on Jun. 12, 2003, 1 page.
Worl Wide Web, http://www.fcs-cs.com/robotics/content/research.htm, "Research," printed on Jun. 12, 2003, 1 page.
World Wide Web, http://www.fcs-cs.com/robotics/content/rehabilitation.htm, "Rehabilitation," printed on Jun. 12, 2003, 1 page.
World Wide Web, http://www.fcs-cs.com/robotics/content/simulation.htm, "Simulation & Training," printed on Jun. 12, 2003, 1 page.
World Wide Web, http://www.fcs-cs.com/robotics/content/reality.htm, "Virtual Reality," printed on Jun. 12, 2003, 1 pages.
World Wide Web, http://www.fcs-cs.com/robotics/content/design.htm, "Virtual Design, Assembly & Maintenance," printed on Jun. 12, 2003, 1 page.
World Wide Web, http://www.fcs-cs.com/robotics/content/assistance.htm, "Surgical Assistance," printed on Jun. 12, 2003, 1 page.
World Wide Web, http://www.merl.com/projects/surgSim99/, "Knee Arthroscopy Simulation," printed on Jun. 12, 2003, 2 pages.
World Wide Web, http://haptics.me.jhu.edu/r.sub.--kine.html, "Robot Design and Kinematics," printed on Jun. 12, 2003, 2 pages.
World Wide Web, http://haptics.me.jhu.edu/r.sub.--hapt.html, "Haptic Interfaces and Virtual Environments," printed on Jun. 12, 2003, 2 pages.
Zilles, et al., "A Constraint-Based God-object Method for Haptic Display", IEEE Proceedings, pp. 146-151, 1995.
Patent Abstracts of Japan for JP 08-215211 from website of Japanese Patent Office (1 page).
Patent Abstracts of Japan for JP 2000-279425 and machine translation of JP 2000-279425 from website of Japanese Patent Office (29 pages).
Patent Abstracts of Japan for JP 2002-102251 and machine translation of JP 2002-102251 from website of Japanese Patent Office (10 pages).
Patent Abstracts of Japan for JP 2003-053684 from website of Japanese Patent Office (1 page).
Office Action for Japanese Application No. 2006-520381, dated May 19, 2010 (3 pages).
English translation of Office Action for Japanese Application No. 2006-520381, dated May 19, 2010 (5 pages).
Office Action for Japanese Application No. 2006-520381, dated Nov. 18, 2010 (3 pages).
English translation of Office Action for Japanese Application No. 2006-520381, dated Nov. 18, 2010 (5 pages).
Office Action for Chinese Application No. 200480023380.5, dated Jul. 18, 2010 (4 pages).
English translation of Office Action for Chinese Application No. 200480023380.5, dated Jul. 4, 2008 (5 pages).
Office Action for Chinese Application No. 200480023380.5, datd Jan. 23, 2009 (5 pages).
English translation of Office Action for Chinese Application No. 200480023380.5, dated Jan. 23, 2009 (7 pages).
International Preliminary Report on Patentability for PCT/US2004/022978 including International Search Report and Written Opinion, dated Feb. 13, 2007 (6 pages).
International Search Report for PCT/US2003/007063, dated Apr. 16, 2004 (7 pages).
International Preliminary Examination Report for PCT/US2003/007063, dated Sep. 2, 2004 (2 pages).
Office Action for U.S. Appl. No. 11/357,197, mail date Sep. 29, 2010, 9 pages.
Applicant's response to Office Action for U.S. Appl. No. 11/357,197, submitted Jan. 31, 2011, 29 pages.
Office Action for U.S. Appl. No. 11/357,197, mail date Apr. 12, 2011, 9 pages.
Applicant's response to Office Action for U.S. Appl. No. 11/357,197, submitted Apr. 15, 2011, 20 pages.
Applicant's request under Rule 48 correcting inventorship for U.S. Appl. No. 11/357,197, submitted Apr. 15, 2011, 2 pages.
T.V. Thompson II, D.E. Johnson & E. Cohen, *Direct haptic rendering of sculptured models*, Proceedings of the Symposium on Interactive 3D Graphics, pp. 167-76, 1997.
K. Salisbury & C. Tar, *Haptic rendering of surfaces defined by implicit functions*, Proceedings of the ASME Dynamic Systems and Control Division, DSC-vol. 61, pp. 61-67, 1997.
E. Colgate, M.C. Stanley & J.M. Brown, *Issues in the haptic display of tool use*, Proceedings of the IEEE/RSJ International Conference on Intelligent Robots and Systems, vol. 3, pp. 140-145, 1995.

\* cited by examiner

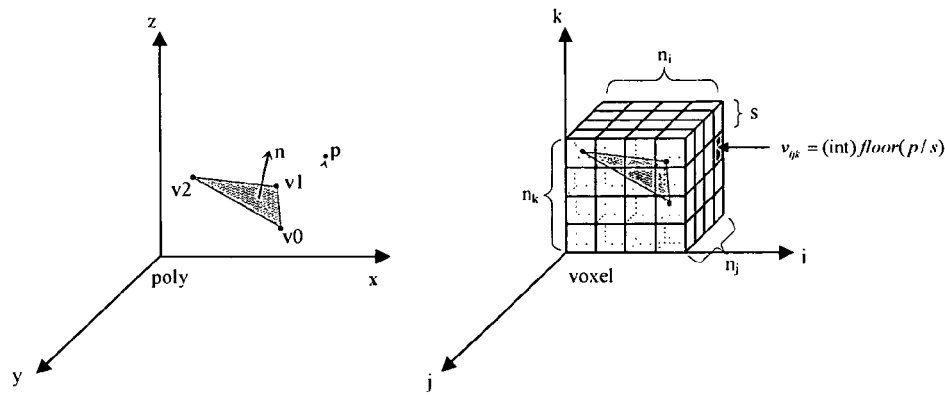
Fig. 6                    Fig. 7
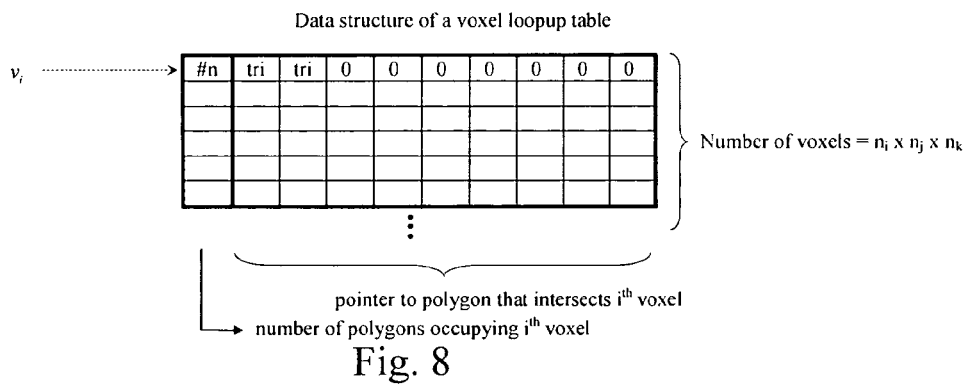
Fig. 8
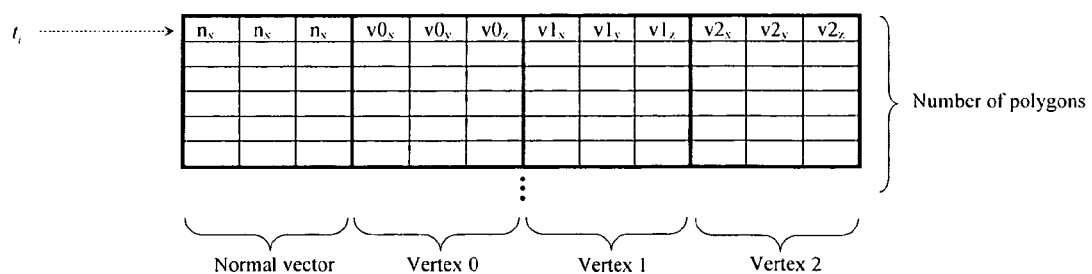
Fig. 9

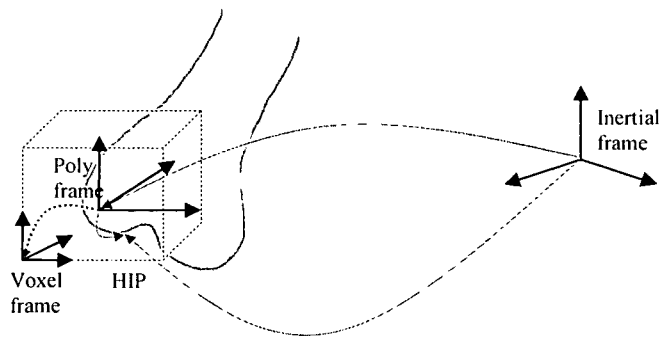
Fig 11
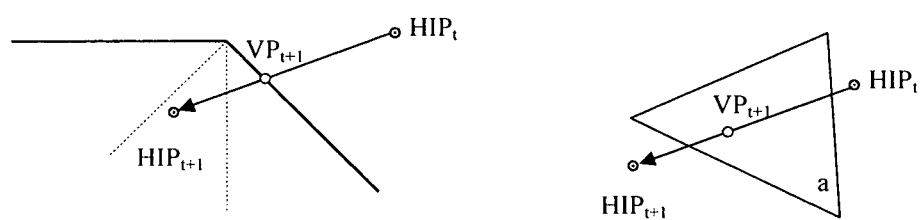
Fig 12
Fig 13

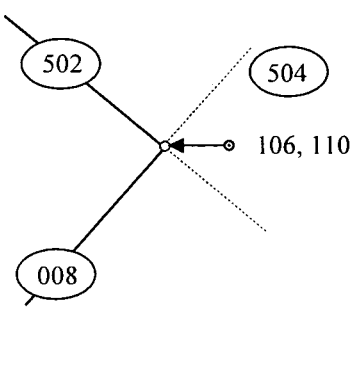
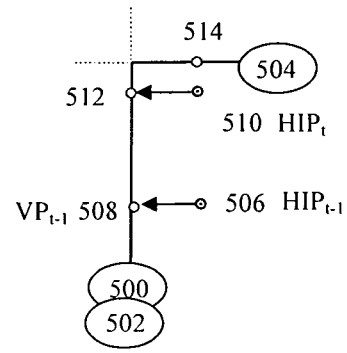
Fig 19
Fig. 20

APPARATUS AND METHOD FOR HAPTIC RENDERING

RELATED APPLICATIONS

This application is a continuation-in-part of U.S. patent application Ser. No. 11/357,197, filed Feb. 21, 2006, published Jun. 29, 2006; the Ser. No. 11/357,197 application is a continuation-in-part of U.S. patent application Ser. No. 10/384,072, filed Mar. 6, 2003, published Feb. 5, 2004; a continuation-in-part of U.S. patent application Ser. No. 10/384,077, filed Mar. 6, 2003, published Feb. 19, 2004; and a continuation-in-part of U.S. patent application Ser. No. 10/384,194, filed Mar. 6, 2003, published Feb. 19, 2004, each of which claims priority from U.S. Provisional Patent Application No. 60/362,368, filed Mar. 6, 2002. The Ser. No. 11/357,197 application is also a continuation-in-part of U.S. patent application Ser. No. 10/621,119, filed Jul. 16, 2003, published Jun. 3, 2004, which is a continuation-in-part of U.S. patent application Ser. No. 10/384,078, filed Mar. 6, 2003, published Feb. 19, 2004, which claims priority from U.S. Provisional Patent Application Ser. No. 60/362,368, filed Mar. 6, 2002. The Ser. No. 11/357,197 application further claims priority from U.S. Provisional Patent Application Ser. No. 60/655,642, filed Feb. 22, 2005, and U.S. Provisional Patent Application Ser. No. 60/759,186, filed Jan. 17, 2006. Each of the above-referenced published applications is incorporated by reference herein in its entirety.

FIELD OF THE INVENTION

The invention relates to a rendering in a robotic system and, more particularly, to rendering in a haptic system.

BACKGROUND

Haptic interfaces permit a user to experience a sense of touch in a virtual or haptic environment. Such interfaces are finding acceptance in virtual reality games and in performing tasks that are virtually imaged. One area which uses virtual images to help a user perform a task is computer aided surgery.

In computer aided surgery, a haptic interface can be used to provide haptic guidance to a surgeon. For example, as the surgeon moves a surgical instrument in real space, constraints may be imposed on the surgeon through the haptic interface that limit his ability to manipulate the surgical instrument. The constraints may be based, for example, upon a desired relationship between a virtual instrument and a haptic object in virtual space. In operation, the surgeon manipulates the surgical instrument robotically using the haptic interface. Constraint feedback is provided to the surgeon through the haptic interface, which imposes a force on the surgeon sufficient to maintain the desired relationship between the virtual instrument and the haptic object.

For example, the haptic object may be a virtual protective boundary for an anatomic structure. The virtual boundary is registered (or correlated) to the anatomy of a patient, and the virtual instrument is registered (or correlated) to the actual surgical instrument. To enable the surgeon to interact with the virtual environment via the haptic interface, a haptic rendering algorithm is employed. Haptic rendering is the process of computing and applying forces in response to user interactions with virtual objects. Using the haptic rendering algorithm, the haptic interface may be configured so that as the virtual instrument approaches the virtual boundary, the force experienced by the surgeon increases. This increasing force provides a warning to the surgeon that he is near the structure of interest and therefore should proceed with caution in order to prevent unwanted penetration into and damage to the structure (for example preventing a drill bit from entering too deeply into a bone).

The present invention addresses this need for an improved haptic rendering process.

SUMMARY OF THE INVENTION

In one aspect, the invention relates to a method for generating a haptic penalty force. In one embodiment, the method includes the steps of: defining a primary proxy position; defining a secondary proxy position; defining a HIP position; generating a first force in response to the primary proxy position and the HIP position when a HIP is positioned at a penetration depth less than or equal to a predetermined value from the primary proxy position; and generating a second force in response to the secondary proxy position and the HIP position when the secondary proxy position is located at a penetration depth greater than the predetermined value from the primary proxy position.

In one embodiment, the predetermined value is a desired haptic offset. In another embodiment, the first force is zero. In yet another embodiment, the second force is a function of a distance between the secondary proxy position and the HIP position. In still yet another embodiment, the first force is a function of a distance between the primary proxy position and the HIP position. In another embodiment, the second proxy position is determined in response, at least in part, to interactions between the HIP and a virtual haptic object. In another embodiment, the penetration depth is a distance between the primary proxy position and the HIP position.

In another aspect, the invention relates to an apparatus for generating a haptic force. In one embodiment, the apparatus includes: a primary proxy position locator for defining a primary proxy position; a secondary proxy position locator for defining a secondary proxy position; a HIP position locator for defining a HIP position; and a force generator for generating a first force in response to the primary proxy position and the HIP position when a HIP is positioned at a penetration depth less than or equal to a predetermined value from the primary proxy position, and generating a second force in response to the secondary proxy position and the HIP position when the secondary proxy position is located at a penetration depth greater than the predetermined value from the primary proxy position.

In another embodiment, the second force is a function of a distance between the secondary proxy position and the HIP position. In yet another embodiment, the first force is a function of a distance between the primary proxy position and the HIP position. In still yet another embodiment, the second proxy position is determined, at least in part, in response to interactions between the HIP and a virtual haptic object.

Yet another aspect of the invention is a method for mapping a location in haptic space. In one embodiment, the method includes the steps of: a) defining a voxel space comprising a plurality of voxel elements; b) defining a polygonal space comprising a plurality of polygonal rendering elements; c) generating a data structure of each of the voxel elements and its respective polygonal rendering elements; d) locating a point in haptic space; e) mapping that point to a corresponding voxel element; and f) selecting, in the data structure, at least one polygonal rendering element.

In one embodiment, the polygonal rendering element is triangular. In another embodiment, each voxel element is an axis aligned box. In yet another embodiment, the data structure is a lookup table.

In yet another aspect, the invention relates to a method for increasing haptic stability in a system having a plurality of transmission mechanisms and a plurality of joints. In one embodiment, the method includes the steps of: calculating a spring force in response to the distance between a proxy position and a HIP position; calculating a joint space spring torque in response to the spring force; calculating a joint space damping torque in response to a joint velocity; and adding the joint space damping torque and the joint space spring torque.

In another embodiment, the spring force is calculated in Cartesian coordinates. In yet another embodiment, the spring force is a function of a difference between the proxy position and the HIP position. In still yet another embodiment, the joint space spring torque is calculated from a Jacobian transpose of the spring force. In another embodiment, the joint space damping torque is a function of the joint velocity. In yet another embodiment, the joint space damping torque is linearly proportional to the joint velocity and a constant of proportionality is calculated in response to diagonal terms of a joint space damping gain matrix. Another aspect of the invention relates to a method of forming a uniphase haptic wall, including the steps of determining from which position a HIP is approaching a boundary and permitting the HIP to pass through the boundary from a first direction and not to pass through the boundary from a second direction.

BRIEF DESCRIPTION OF THE DRAWINGS

Reference to the figures herein is intended to provide a better understanding of the methods and apparatus of the invention but is not intended to limit the scope of the invention to the specifically depicted embodiments. The drawings are not necessarily to scale, emphasis instead being placed upon illustrating the principles of the invention. Like reference characters in the respective figures typically indicate corresponding parts.

FIG. 6 is a representation of an embodiment of a polygon surface object according to the present invention;

FIG. 7 is a representation of an embodiment of a voxel map according to the present invention;

FIG. 8 is a representation of an embodiment of a voxel lookup table according to the present invention;

FIG. 9 is a representation of an embodiment of a polygon lookup table according to the present invention;

FIG. 11 is a graphical illustration of a coordinate transformation;

FIG. 12 is an illustration of a virtual proxy point location;

FIG. 13 is an illustration of a virtual proxy point location;

FIG. 19 is a pictorial representation of an x-y view of an augmenting concave corner behavior;

FIG. 20 is a pictorial representation of a y-z view of an augmenting concave corner behavior;

DETAILED DESCRIPTION

Figure 1:
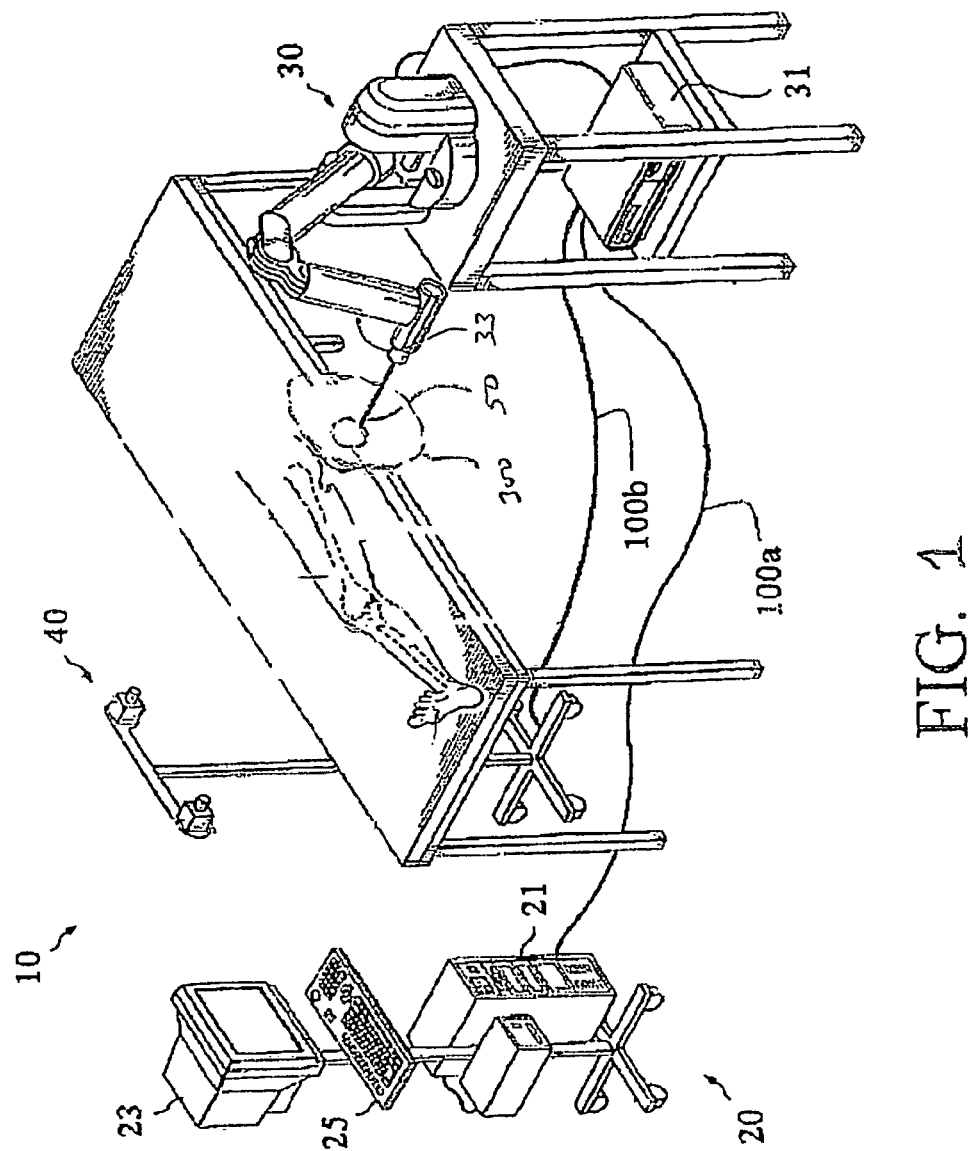
FIG. 1 is a perspective view of an embodiment of a surgical system according to the present invention.

In brief overview, FIG. 1 shows an embodiment of a surgical system 10 according to the present invention. The surgical system 10 includes a computing system 20, a haptic robotic device 30, and a tracking (or localizing) system 40. In operation, the surgical system 10 enables comprehensive, intraoperative surgical planning. The surgical system 10 also provides haptic guidance to a user (e.g., a surgeon) and/or limits the user's manipulation of the haptic device 30 as the user performs a surgical procedure.

The computing system 20 includes hardware and software for operation and control of the surgical system 10. As shown in FIG. 1, the computing system 20 includes a computer 21, a display device 23, and an input device 25.

The computer 21 may be any known computing system, but is preferably a programmable, processor-based system. For example, the computer 21 may include a microprocessor, a hard drive, random access memory (RAM), read only memory (ROM), input/output (I/O) circuitry, and any other well-known computer component. The computer 21 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 21 may include one or more independent or networked computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably including a graphical user interface (GUI). In one embodiment, the computer 21 includes a Navigation Module available from MAKO SURGICAL CORP™, Fort Lauderdale, Fla.

The display device 23 is a visual interface between the computing system 20 and the user. The display device 23 is connected to the computer 21 and may be any device suitable for displaying text, images, graphics, and/or other visual output. For example, the display device 23 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 23 may be disposed on or near the computer 21 or may be remote from the computer 21 at any location well-suited for ease of viewing by the user. The display device 23 may be used to display any information useful for a medical procedure, including but not limited to, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

In addition to the display device 23, the computing system 20 may include an acoustic device (not shown) for providing audible feedback to the user. The acoustic device is connected to the computer 21 and may be any device for producing sound. For example, the acoustic device may include speakers and a sound card, a motherboard with integrated audio support, and/or an external sound controller. In operation, the acoustic device may be adapted to convey information to the user. For example, the computer 21 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 25 of the computing system 20 enables the user to communicate with the surgical system 10. The input device 25 is connected to the computer 21 and may include any device enabling a user to provide input to a computer. For example, the input device 25 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 20 is adapted to enable the surgical system 10 to perform various functions related to surgical planning, navigation, image guidance, and/or haptic guidance. For example, the computer 21 may include algorithms, programming, and software utilities related to general operation, data storage and retrieval, computer aided surgery (CAS), applications, haptic control, and/or any other suitable functionality. In one embodiment, the computing system 20 includes software used in a Navigation Module.

Utilities related to general operation are configured to provide basic computing functions that enable and support overall operation of the surgical system 10. General operation utilities may include, for example, well known features such as functions for fast graphics processing, functions for supporting input/output (I/O) devices, functions for connecting to a hospital network, functions for managing database libraries (e.g., implant and instrument databases), functions for system security (e.g., login features, access restrictions, etc.), and/or any other functionality useful for supporting overall operation of the surgical system 10.

Utilities related to data storage and retrieval are configured to enable storage of and access to various forms of data, such as image data (e.g., two- or three-dimensional image data sets obtained using any suitable imaging modality, such as, for example, x-ray, computed tomography (CT), magnetic resonance (MR), positron emission tomography (PET), single photon emission computed tomography (SPECT), ultrasound, etc.), application data, implant data, instrument data, anatomical model data, patient data, user preference data, and the like. The data storage and retrieval utilities may include any functionality appropriate for storing and handling relevant data.

Utilities related to computer aided surgery are configured to enable surgical planning, navigation, and basic image guided surgery capabilities. For example, as is well known, the CAS utilities may include functions for generating and displaying images from image data sets, functions for determining a position of a tip and an orientation of an axis of a surgical instrument, and functions for registering a patient and an image data set to a coordinate frame of the tracking system 40. These functions enable, for example, the computing system 20 to display on the display device 23 a virtual representation of a tracked surgical instrument overlaid on one or more images of a patient's anatomy and to update the virtual representation of the tracked instrument in real time during a surgical procedure. Images generated from the image data set may be two-dimensional or, in the case of a three-dimensional image data set, a three-dimensional reconstruction based, for example, on segmentation of the image data set. When more than one image is shown on the display device 23, the computing system 20 preferably coordinates the representation of the tracked instrument among the different images. In addition to or in lieu of images generated from image data sets, the computing system 20 may use anatomical models (e.g., based on CAD models, line art, sketches, cartoons, artist renderings, generic or morphed data sets, etc.).

Utilities related to applications of the surgical system 10 include application specific programs configured to assist the user with surgical planning and navigation. Programs associated with the application utilities may be configured for use in various medical procedures and/or may be customized for a specific procedure. For example, the application utilities may include programs related to one or more orthopedic procedures, such as, for example, total knee replacement, partial knee replacement, hip replacement, shoulder replacement, elbow replacement, wrist replacement, ankle replacement, spinal surgery, and/or installation of orthopedic and/or musculoskeletal implants, including implants of conventional materials and more exotic implants, such as orthobiologics, drug delivery implants, and cell delivery implants. The application utilities may be directed to various aspects of surgical planning and navigation, including pre-operative, intra-operative, and post-operative activities. For example, the application utilities may include programs or processes directed to planning and set up, such as, for example, system initialization processes, planning processes, visualization processes, diagnostic imaging processes, registration processes, and calibration processes. The application utilities may also include programs or processes directed to object tracking and system control, such as, for example, coordinate transform processes, interpolation processes, tool and power control processes, anatomy positioning processes, mode control processes, safety processes, occlusion detection algorithms, and forward kinematics algorithms. The application utilities may include programs or processes related to the haptic device 30, such as, for example, haptic force computation processes, haptic force mapping processes, processes for generating haptic objects, and haptic rendering algorithms. The application utilities may also include programs and processes for communicating with the user during a surgical procedure, such as, for example, software for displaying pages or images corresponding to specific steps of a surgical procedure, software for prompting a user to perform a certain task, and software for providing feedback (e.g., visual, audible, tactile, and/or force feedback) to the user.

Utilities related to haptic control are configured to perform various functions related to control, performance, stability, and/or safety of the haptic device 30. For example, the haptic control utilities may include a real time operating system (RTOS), motion control software, hardware and software for generating high frequency updates for control of the haptic device 30, software for ensuring fail-safe operation of the haptic device 30 (e.g., control of brakes, monitoring of redundant sensors, etc.), and/or any other utility suitable for improving or promoting performance, stability, and/or safety of the haptic device 30. The haptic control utilities may be executed on the computer 21 of the computing system 20 provided the computer 21 has a computing architecture sufficient to support the operating requirements of the haptic control utilities. The computer 21 may be free-standing or incorporated into the robot stand or arm. For example, processes associated with haptic control typically have higher operational frequency requirements than other processes running on the computer 21. In one embodiment, the haptic control processes operate at a frequency of approximately 2 kHz. In another embodiment, the haptic control processes operate at a frequency in a range of between about 0.1 kHz to about 10 kHz. In yet another embodiment, the haptic control processes operate at a frequency in a range of between about 500 Hz to about 2,400 Hz. In other embodiments, the computer 21 supplies control information suitable for obtaining the operating frequency required by the haptic control processes (e.g., approximately 2 kHz). In a preferred embodiment, the computer 31 is integrated or embedded with the haptic device 30. If the computer 21 does not have an architecture sufficient to support operation of the haptic control processes, the computing system 20 may include a supplemental computer 31 for execution of the haptic control utilities.

The computer 31 (shown in FIG. 1) may be similar to the computer 21, but is preferably configured to satisfy specific operational requirements of the haptic device 30, such as, for example, the need for providing control information at the operating frequencies of the haptic device 30. The computer 31 may further comprise one or more independent or networked computers. In one embodiment, the computer 31 is an Intel compatible x86 3U CompactPCI single-board computer with a processor clock speed of at least 1.6 GHz, at least 2 GByte of non-volatile storage (e.g., hard disk drive, Compact FLASH, etc.), at least 256 MB of RAM, 400 MHz Front Side Bus or faster, at least 1 MByte of Level 2 cache memory, and a real-time operating system. One such commercially available embodiment includes the ICP-PM-1004-DG-8A computer from Inova Computers GmbH (Kaufbeuren, Germany), used with the QNX 6.1 (or later) operating system from QNX Software Systems Ltd. (Ottawa, Ontario, Canada).

In addition to the haptic control utilities, the computer 31 may include programs that enable the haptic device 30 to utilize data from the tracking system 40. For example, the tracking system 40 may generate tracked object pose (e.g., position and orientation) data periodically. In one embodiment, the object pose data is generated at approximately 30 Hz. In other embodiments, object pose data is generated more frequently such as, for example, at approximately 500 Hz or greater. The object posed data is transferred from the tracking system 40 to the computer 31 (e.g., via an interface 100b) and may be conditioned in any conventional manner such as, for example, using a noise filter as is well known. Additionally, in embodiments where the tracking system 40 operates at a lower frequency than the haptic control processes, the object pose data may be conditioned using an interpolation filter as is well known. The interpolation filter smoothes the object pose data by populating gaps between discrete data samples to enable the object pose data to be used in the higher frequency haptic control processes. The computer 31 may also include a coordinate transform process for mapping (or transforming) coordinates in one space to those in another to achieve spatial alignment or correspondence. For example, the surgical system 10 may use the coordinate transform process to map positions of tracked objects (e.g., surgical tools, patient anatomy, etc.) into a coordinate system used by a process running on the computer 31 and/or the computer 21. As is well known, the coordinate transform process may include any suitable transformation technique, such as, for example, rigid-body transformation, non-rigid transformation, affine transformation, and the like.

One advantage of including multiple computers (e.g., the computer 21 and the computer 31) in the computing system 20 is that each computer can be independently configured. Thus, the computer 21 can be customized for surgical planning and navigation, and the computer 31 can be customized for controlling performance, stability, and/or safety of the haptic device 30. For example, the computer 31 may include a real time operating system (RTOS) to maintain dependable updates to the haptic control system and a stable operating platform for the haptic device 30. In contrast, the computer 21 may include a non-RTOS because the computing system 20 may not require the same degree of stability as the haptic device 30. Thus, the computer 21 may instead be customized to meet specific requirements of surgical navigation, such as, for example, graphics processing.

Another advantage of multiple computers having separate computing architectures is that software developers with limited knowledge of haptic systems can create CAS utilities for the computer 21 that can be used in conjunction with a variety of haptic devices. Similarly, software developers with limited knowledge of CAS can create haptic utilities focused on enhancing the performance, stability, and/or safety of a particular haptic device. As an alternative to separate computers, the computing functions of the haptic device 30 and the computing system 20 may be incorporated, for example, into a single computer, into the computing system of an imaging device (e.g., a CT device, an MRI device, a fluoroscopic device, etc.), and/or into a hospital networked computing system.

As shown in FIG. 1, the computing system 20 is coupled to the haptic device 30 via an interface 100a. The interface 100a includes a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 21 and/or the computer 31 and enables the computing system 20 to communicate with and control operation of the haptic device 30. In one embodiment, the software interface includes a utility that allows the computing system 20 to issue commands to the haptic device 30. For example, the computer 21 may send a command to the computer 31 requesting the haptic device 30 to enter a specific mode (e.g., approach mode, haptic mode, free mode, input mode, hold mode). In response, the computer 31 may be programmed to check various parameters to verify that entry into the requested mode is safe and otherwise acceptable and to either enter the haptic device 30 into the requested mode or return an appropriate error message.

The haptic device 30 is a surgical device configured to be manipulated by a user to move a surgical tool 50 to perform a procedure on a patient. During the procedure, the computing system 20 implements control parameters for controlling the haptic device 30 based, for example, on a relationship between an anatomy of the patient and a position, an orientation, a velocity, and/or an acceleration of a portion of the surgical tool 50. In one embodiment, the haptic device 30 is controlled to provide a limit on user manipulation of the device (e.g., by limiting the user's ability to physically manipulate the haptic device 30). In another embodiment, the haptic device 30 is controlled to provide haptic guidance (i.e., tactile and/or force feedback) to the user. Tactile feedback generally includes tactile sensations such as, for example, vibration, whereas force feedback refers to feedback in the form of force (e.g., resistance to movement) and/or torque (also known as "wrench). Wrench includes, for example, feedback in the form of force, torque, or a combination of force and torque.

Guidance from the haptic device 30 coupled with computer aided surgery (CAS) enables a surgeon to actively and accurately control surgical actions (e.g., bone cutting) and delivery of localized therapies (e.g., in the brain). For example, the computing system 20 may be programmed to determine the control parameters based on data representative of a patient's anatomy (e.g., preoperative CT image data, ultrasound data); a virtual (or haptic) object associated with (or registered to) the anatomy; a parameter relative to the anatomy (e.g., a depth defined with respect to a portion of the anatomy); and/or the anatomy. The computing system 20 can control the haptic device 30 to generate a force, a torque, and/or vibration based on the position of the tool 50 relative to the virtual object, the parameter, and/or the anatomy. For example, the tool 50 may be constrained against penetrating a virtual boundary associated with a representation of the anatomy and/or constrained against exceeding a parameter defined with respect to the representation of the anatomy. Thus, in operation, as a surgeon manipulates the haptic device 30 to move the tool 50, virtual pathways may be used to guide the tool 50 to specific targets, virtual boundaries may be used to define cutting shapes or to prevent the tool 50 from contacting critical tissue, and predefined parameters may be used to limit travel of the tool 50 (e.g., to a predefined depth).

The computing system 20 may also be programmed to adjust the control parameters in response to movement of the physical anatomy during the procedure (e.g., by monitoring detected movement of the physical anatomy and then adjusting the virtual object in response to the detected movement). In this manner, the surgical system 10 can supplement or replace direct visualization of the surgical site, enhance the surgeon's natural tactile sense and physical dexterity, and facilitate the targeting, repairing, and replacing of various structures in the body through conventionally sized portals (e.g., 12 inches or greater in length) to portals having a diameter as small as approximately 1 mm.

In orthopedic applications, for example, the haptic device 30 can be applied to the problems of inaccuracy, unpredictability, and non-repeatability in bone preparation by assisting the surgeon with proper sculpting of bone to thereby enable precise, repeatable bone resections while maintaining intimate involvement of the surgeon in the bone preparation process. Moreover, because the haptic device 30 haptically guides the surgeon in the bone cutting operation, the skill level of the surgeon is less critical. As a result, surgeons with varying degrees of skill and experience are able perform accurate, repeatable bone resections. In one embodiment, for example, a surgical tool is coupled to the haptic device 30. The surgeon can operate the tool to sculpt bone by grasping and moving the tool and/or by grasping and manipulating the haptic device 30 to move the tool. As the surgeon performs the cutting operation, the surgical system 10 tracks the location of the tool (with the tracking system 40) and, in most cases, allows the surgeon to freely move the tool in the workspace. When the tool is in proximity to a virtual boundary in registration with the patient, however, the surgical system 10 controls the haptic device 30 to provide haptic guidance that tends to constrain the surgeon from penetrating the virtual boundary with the tool. For example, the virtual boundary may be defined by a haptic object, and the haptic guidance may comprise an output wrench (i.e., force and/or torque) that is mapped to the haptic object and experienced by the surgeon as resistance to further tool movement in the direction of the virtual boundary. Thus, the surgeon may feel as if the tool has encountered a physical object, such as a wall. In this manner, the virtual boundary functions as a virtual cutting guide. Thus, the haptic device 30 communicates information to the surgeon regarding the location of the tool relative to the virtual boundary and provides physical guidance in the actual cutting process. The haptic device 30 may also be configured to limit the user's ability to manipulate the surgical tool as described, for example, in U.S. patent application Ser. No. 10/470,314 (Pub. No. US 2004/0128026), which is owned by the assignee of the present invention and is hereby incorporated by reference herein in its entirety.

The haptic device 30 may include a mechanical or electromechanical device adapted to transmit tactile feedback (e.g., vibration) and/or force feedback (e.g., wrench) to the user. The haptic device 30 may be robotic, non-robotic, or a combination of robotic and non-robotic systems. For example, the haptic device 30 may include a haptic device as described in U.S. patent application Ser. No. 10/384,072, filed Mar. 6, 2003, published Feb. 5, 2004; U.S. patent application Ser. No. 10/384,077, filed Mar. 6, 2003, published Feb. 19, 2004; U.S. patent application Ser. No. 10/384,078, filed Mar. 6, 2003, published Feb. 19, 2004; U.S. patent application Ser. No. 10/384,194, filed Mar. 6, 2003, published Feb. 19, 2004; U.S. patent application Ser. No. 10/621,119, filed Jul. 16, 2003, published Jun. 3, 2004; and/or U.S. Provisional Patent Application Ser. No. 60/655,642, filed Feb. 22, 2005. Each of the above-referenced published applications is owned by the assignee of the current application and is hereby incorporated by reference herein in its entirety.

In operation, the computing system 20, the haptic device 30, and the tracking system 40 cooperate to enable the surgical system 10 to provide haptic guidance to the user during a surgical procedure. The surgical system 10 provides haptic guidance by simulating the human tactile system using a force feedback haptic interface (i.e., the haptic device 30) to enable the user to interact with a virtual environment. The haptic device 30 generates computer controlled forces to convey to the user a sense of natural feel of the virtual environment and virtual (or haptic) objects within the virtual environment. The computer controlled forces are displayed (i.e., reflected or conveyed) to the user to make him sense the tactile feel of the virtual objects. For example, as the user manipulates the tool 50, the surgical system 10 determines the position and orientation of the tool 50. Collisions between a virtual representation of the tool 50 and virtual objects in the virtual environment are detected. If a collision occurs, the surgical system 10 calculates haptic reaction forces based on a penetration depth of the virtual tool into the virtual object. The calculated reaction forces are mapped over the virtual object surface and appropriate force vectors are fed back to the user through the haptic device 30.

As used herein, the term "virtual object" (or "haptic object") can be used to refer to different objects. For example, the virtual object may be a representation of a physical object, such as an implant or surgical tool. Alternatively, the virtual object may represent material to be removed from the anatomy, material to be retained on the anatomy, and/or anatomy (or other objects) with which contact with the tool 50 is to be avoided. The virtual object may also represent a pathway, a guide wire, a boundary, a border, or other limit or demarcation.

Figure 2:
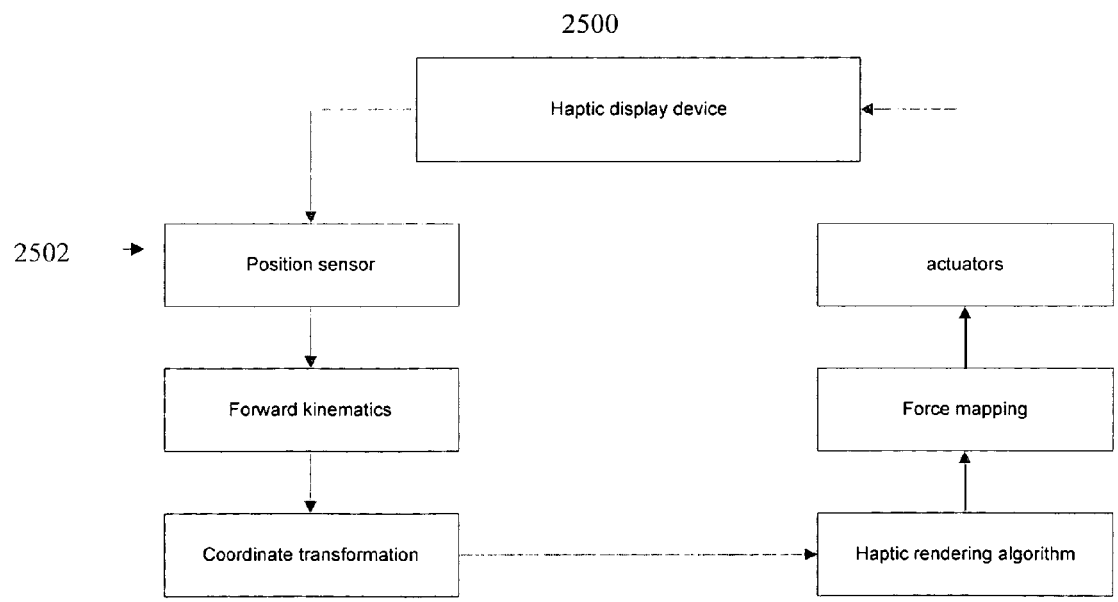
FIG. 2 is a block diagram of an embodiment of a haptic rendering process according to the present invention.

To enable the user to interact with the virtual environment, the surgical system 10 employs a haptic rendering process. Haptic rendering is the process of computing and applying forces in response to user interactions with virtual objects. In one embodiment, the data flow for performing such a process is represented graphically in FIG. 2. In operation, in general, position sensors (block 2502) of the haptic device 30 (block 2500) provide data to a software module, the forward kinematics process (block 2504). Output of the forward kinematics process is input to a coordinate transformation process (block 2506). A haptic rendering algorithm (block 2508) receives data from the coordinate transformation process and provides input to a force mapping process (block 2510). Based on the results of the force mapping process, actuators (block 2512) of the haptic device 30 are actuated to convey an appropriate haptic wrench (i.e., force and/or torque) to the user. The position sensors of block 2502 and the actuators of block 2512 are described above in connection with the arm 33 of the haptic device 30 in FIG. 1. The forward kinematics process of block 2504 and the coordinate transform process of block 2506 are discussed in more detail below in connection with step S708 of FIG. 5. The haptic rendering algorithm of block 2508 and the force mapping process of block 2510 are discussed below.

The haptic rendering process may include any suitable haptic rendering process, such as, for example, a haptic rendering process as described in U.S. Pat. No. 6,111,577; C. B. Zilles & J. K. Salisbury, "A constraint-based god-object method for haptic display," *Proceedings of the IEEE/RSJ International Conference on Intelligent Robots and Systems*, Vol. 3, pp. 146-51, 1995; T. V. Thompson II, D. E. Johnson & E. Cohen, "Direct haptic rendering of sculptured models," *Proceedings of the Symposium on Interactive 3D Graphics*, pp. 167-76, 1997; K. Salisbury & C. Tar, "Haptic rendering of surfaces defined by implicit functions," *Proceedings of the ASME Dynamic Systems and Control Division*, DSC-Vol. 61, pp. 61-67, 1997; and/or J. E. Colgate, M. C. Stanley & J. M. Brown, "Issues in the haptic display of tool use," *Proceedings of the IEEE/RSJ International Conference on Intelligent Robots and Systems*, Vol. 3, pp. 140-45, 1995, each of which is hereby incorporated by reference herein in its entirety.

The virtual environment created by the haptic rendering process includes virtual (or haptic) objects that interact with a virtual representation of the tool 50. Interaction between the virtual objects and the virtual representation of the tool 50 may be point-based or ray-based. In a preferred embodiment, the surgical system 10 employs point-based haptic interaction where only a virtual point, or haptic interaction point (HIP), interacts with virtual objects in the virtual environment. The HIP corresponds to a physical point on the haptic device 30, such as, for example, a tip of the tool 50. The HIP is coupled to the physical point on the physical haptic device 30 by a virtual spring/damper model. The virtual object with which the HIP interacts may be, for example, a haptic object 705 (shown in FIG. 3) having a surface 707 and a haptic force normal vector Fn. A penetration depth $d_i$ is a distance between the HIP and the nearest point on the surface 707. The penetration depth $d_i$ represents the depth of penetration of the HIP into the haptic object 705 and determines, in part, the force $F_n$ experienced by the user of the haptic device.

The virtual (or haptic) objects can be modeled, for example, using 3D geometric primitive objects, 3D polygonal objects, mathematical equations, computer models, surface models, and/or voxel arrays. Haptic objects may be static, quasi-static, dynamic, continuous, discontinuous, time varying, and/or existing only at certain times. In one embodiment, the haptic object is modeled using one or more functions of tool position, orientation, velocity, and/or acceleration. Thus, in the case of a surgical bone cutting operation, the haptic rendering process may produce a mapping of output wrench versus tool position. The mapping may be configured so that the output wrench fed back to the user is sufficient to resist further penetration of the virtual tool (or HIP) into the haptic object. In this manner, a virtual cutting boundary is established. This virtual cutting boundary is associated with (e.g., registered to) the physical anatomy of the patient, an image of the anatomy, and/or other coordinate frame of interest. A haptic object rendered by the haptic rendering process may function as a pathway (e.g., a guide wire), may be repulsive (e.g., configured to repel the tool 50 from entering an interior of a haptic object), may function as a container (e.g., to maintain the tool 50 within the interior of the haptic object), and/or may have portions that repel and portions that contain.

Figure 4:
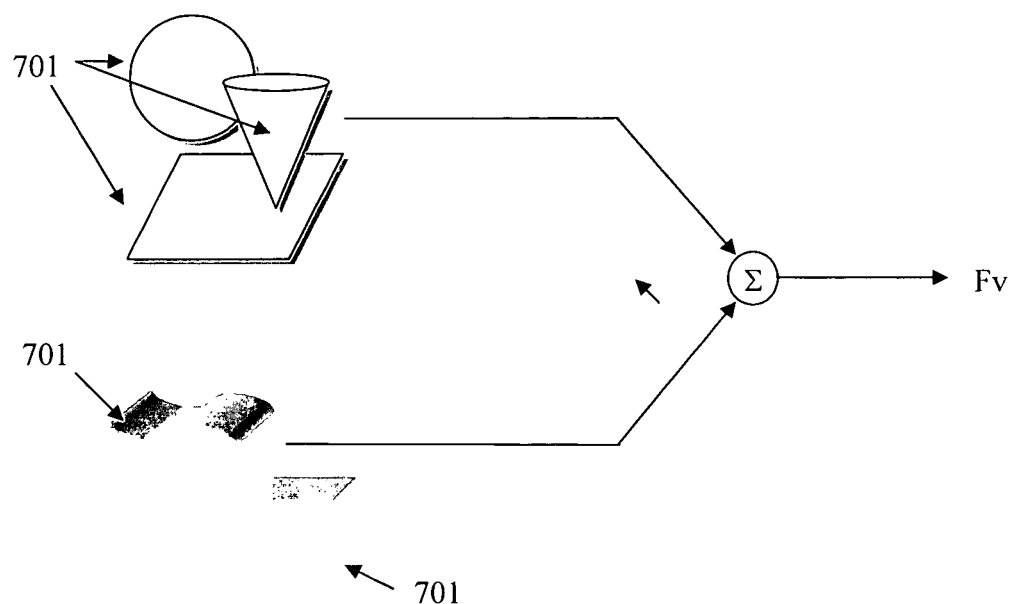
FIG. 4 is a representation of multiple haptic objects that are superimposed.

As shown in FIG. 4, multiple haptic objects 701 may be superimposed so that force vectors F from each of the haptic objects 701 are combined to yield a resultant haptic force vector Fv. In one embodiment, the output from each haptic object 701 comprises a Cartesian force vector with respect to an inertial coordinate frame and having linear properties. The maximum number of haptic objects may be determined based on computational costs.

A haptic object may be customized to include any desired shape, such as, for example, anatomically contoured implant shapes, protective boundaries for sensitive structures (e.g., intra-articular anatomy), image-derived tumor boundaries, and virtual fixtures for in vivo assembly of implant components. In one embodiment, the haptic object may be uniquely contoured to match a disease state of the patient. For example, the haptic object may define a virtual cutting boundary that encompasses only diseased bone. Thus, the haptic object can be used to guide the user in removing the diseased bone while sparing healthy surrounding bone. In this manner, the surgical system 10 enables the user to sculpt bone in a customized manner, including complex geometries and curves that are not possible with conventional cutting jigs and saw guides. As a result, the surgical system 10 facilitates bone sparing surgical procedures and implant designs that are smaller in size and adapted for a patient's unique disease state.

A haptic object may have an associated spatial or geometric representation that can be graphically represented on the display device 23. The graphical representation may be selected so as to convey useful information to the user. For example, as shown in FIG. 1, a haptic object 300 configured assist the user in guiding the tool 50 to the surgical site may be represented graphically as a funnel shaped volume. As a virtual tool corresponding to the physical tool 50 moves through and interacts with the haptic object 300, haptic forces are reflected to the user so that the tool 50 is guided to the surgical site. Alternatively, a haptic object may be represented graphically as a guide wire. As the virtual tool moves along and interacts with the haptic object, haptic forces are reflected to the user so that the tool 50 is guided directly to the surgical site along the guide wire. In one embodiment, a haptic object defining a virtual cutting boundary for an implant may be depicted on the display device 23 as a graphical image having a shape that substantially corresponds to a shape of the implant. Thus, a haptic object defining a virtual cutting boundary for a femoral component will have a corresponding graphical representation. Similarly, a haptic object defining a virtual cutting boundary for a tibial component will have a different corresponding graphical representation.

Figure 3:
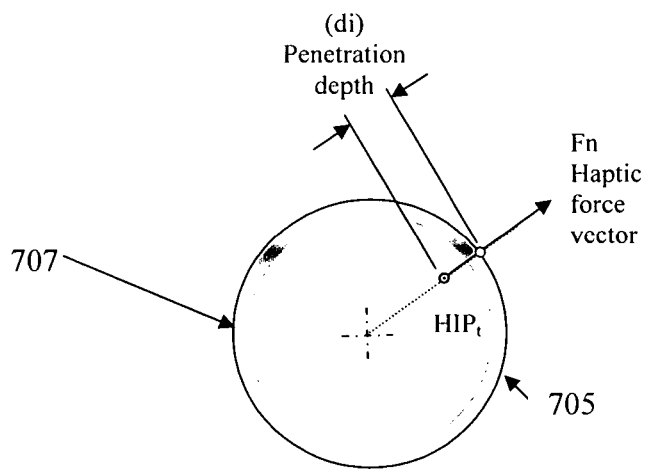
FIG. 3 is a representation of an embodiment of a 3D geometric haptic object according to the present invention.

Haptic objects having simple volumes are preferably modeled with a combination of 3D implicit surface objects such as planes, spheres, cones, cylinders, etc. For example, the haptic object 705 shown in FIG. 3 is a sphere. Surfaces of the haptic object 705 are continuously smooth, and solutions to the penetration depth ($d_i$) and the haptic force vector (Fn) normal to the surface of the object can be obtained at a non-expensive, fixed computational cost from compact mathematical surface functions based on the haptic interaction point (HIP). For more complex objects, polygon based haptic rendering techniques may be used.

Figure 5:
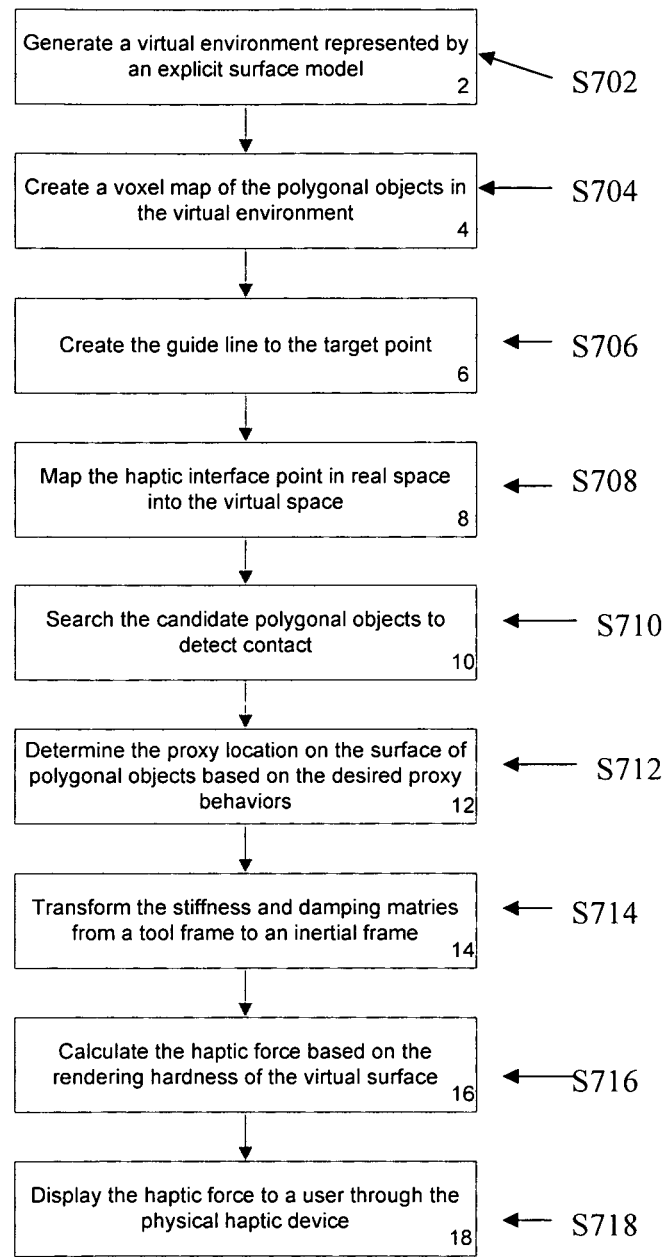
FIG. 5 is a flow diagram of an embodiment of a polygon based haptic rendering process according to the present invention.

FIG. 5 illustrates an embodiment of a polygon based haptic rendering process according to the present invention. In step S702, a virtual environment with which the user can interact is generated using, for example, computer-aided design (CAD) software. The virtual environment may be created, for example, using an explicit surface model. In one embodiment, the virtual environment includes a 3D virtual (or haptic) object comprising multiple polygonal surface objects. As shown in FIG. 6, each surface object is preferably triangular and represented by three nodes (or vertices) v0, v1, and v2 and a normal vector n. The virtual object can be re-shaped to compensate for a physical diameter of the tool 50, for example, by offsetting the walls of the virtual object by a radius of the tool 50. To improve computational performance, which is important in real-time applications, the polygonal surface objects can be re-meshed, for example, to eliminate polygons smaller than a desired spatial resolution. When the virtual object is a closed cavity, creation of the virtual object using a CAD system may be simplified by generating the virtual object with two surfaces: an outer object surface and an inner cavity surface. Using only the inner cavity surface, however, may advantageously reduce the required volume for rendering and the number of polygonal objects (e.g., triangles, polygons, etc.). Furthermore, a unifaced closed virtual cavity may be generated by creating a virtual solid object using a CAD system, generating the surface meshes and inverting the surface such that the normal vector of each polygonal object faces inward. In one embodiment, the rendering process can support uni-directional entrance behavior to a closed virtual object, where the HIP is permitted to pass through the virtual object only if it is moving from outside to inside.

Returning to FIG. 5, in step S704 the haptic rendering process creates a voxel map of the polygonal surface objects in the virtual environment. To create the voxel map, the virtual objects in the virtual environment are spatially partitioned into smaller cells or volume elements (voxels) to reduce the number of polygonal surface objects and avoid unnecessary collision detection checks. As shown in FIG. 7, the virtual objects are segmented into an $n_i \times n_j \times n_k$ grid. The grid may be regularly spaced or may vary in resolution. Each voxel has a pointer to the polygons that occupy or intersect the voxel. Given a set of polygons, a voxel lookup table is constructed by the following steps: retrieve the polygon data (i.e., the xyz components for the vertices v0, v1, and v2) for a polygon of interest; create a bounding box around the polygon; add a unique identity number for the polygon to the voxels that are within the bounding box; and increase the total number of polygons occupying the voxel. These steps are repeated until the last polygon is processed. As shown in FIG. 6 (polygon reference frame) and FIG. 7 (voxel reference frame), a point (p) in the polygon frame is converted into the voxel frame using the formula $v_{ijk} = (int)floor(p/s)$, where s is voxel size. Examples of voxel and polygon lookup tables are presented in FIGS. 8 and 9, respectively.

Figure 10:
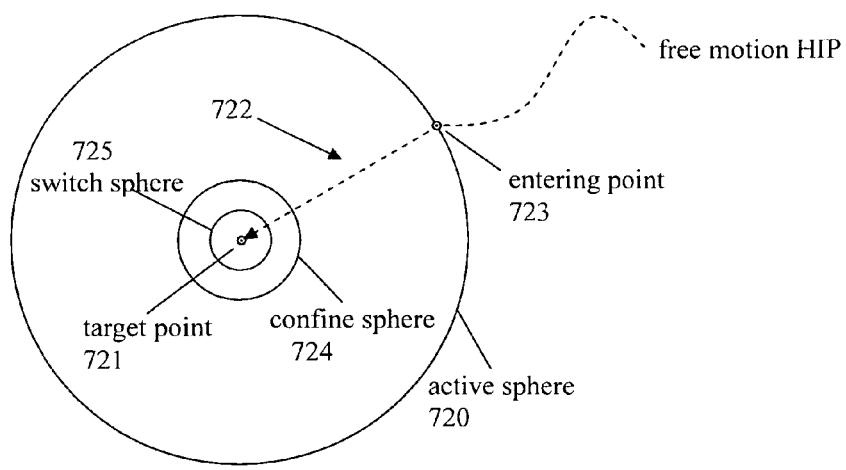
FIG. 10 illustrates an implementation of an embodiment of a virtual guide line according to the present invention.

In step S706 of FIG. 5, the haptic rendering process creates a guide line to a target point or a target region. The guide line functions as a pathway or virtual guide wire that guides the HIP to a particular location. A guide line is useful, for example, to guide the user's movement of the physical tool 50 so that the tool 50 avoids critical anatomy. A guide line is also useful with a closed haptic volume that the user is unable to traverse. Implementation of a guide line is explained with reference to FIG. 10, which illustrates a virtual sphere 720.

The sphere 720 includes an active zone defined by a center 721 and a radius 722 of the sphere 720. When the HIP is outside the active zone, the user can freely move the haptic device 30. When the HIP enters the active zone, the haptic device 30 is placed in an approach mode in which a guiding line segment along a radius 722 is created. The guiding line segment 722 extends, for example, from an entering point ($P_e$) 723 on a surface of the sphere 720 to a target point ($P_t$) 721. Normally, the center of the sphere 720 will be coincident with the target point (or at least will be within a target region). When the guiding line segment 722 is activated, the HIP can move freely along the guiding line segment 723. Motion of the HIP that deviates from the guiding line segment 722 (e.g., due to attempted motion perpendicular to the guiding line segment 722), results in a resisting force that is fed back to the user. As the HIP approaches the target point, a distance from a current location of the HIP to the target point is monitored. When the distance is smaller than a confine radius, the behavior of the HIP is restricted, for example, by implementing a uni-directionally constrained virtual confining sphere 724. A radius of the confining sphere 724 is reduced as the HIP moves closer to the target point. When the distance from the HIP to the target point is smaller than a switch radius (represented in FIG. 10 by a switch sphere 725), haptic rendering of the virtual object begins.

In step S708 of FIG. 5, the haptic rendering process maps the physical HIP (e.g., the tip of the tool 50) to virtual space. For example, the forward kinematics process (block 2504) of FIG. 2 computes a Cartesian position of the physical HIP with respect to an inertial reference frame (Ri). The coordinate transformation process (block 2506) of FIG. 2 performs coordinate transformations between the inertial reference frame (Ri), a polygon frame (Rp) (a reference frame attached to a polygonal virtual object), and a voxel frame (Rv) (a reference frame attached to a voxel array) as illustrated in FIG. 11. Once the haptic rendering process has determined the position of the HIP with respect to the polygonal object reference frame (Rp), the haptic rendering process proceeds to step S710 and searches candidate polygonal objects by looking at occupied voxels and neighboring voxels. In step S712, the haptic rendering process checks for a collision (e.g., the HIP has passed through a polygonal object since the last rendering cycle) and determines a virtual proxy point location (e.g., a constrained location of the HIP along a surface of the virtual object) based on desired virtual proxy behaviors (as described below in connection with FIGS. 12, 13). In step S714, desired stiffness and damping matrices that are predefined in tool coordinates are transformed into inertial reference frame coordinates. In step S716, a haptic force to be fed back to the user through the haptic device 30 is computed based on a desired hardness of a virtual surface defined by the virtual spring and damping force that couples the HIP to the haptic device 30. In step S718, the computed haptic force is displayed or reflected to the user through the haptic device 30.

As shown in FIGS. 12 and 13, a location of an initial virtual proxy point may be determined based on a location (HIP(t)) of the HIP at a current time t and a location (HIP(t−1)) of the HIP at a previous time (t−1). For example, when the HIP is outside a virtual object, the haptic rendering process checks for an initial contact between the HIP and a surface of the virtual object by detecting an intersection between the polygonal surface objects that comprise the virtual object and a line segment (L) extending between the locations HIP(t) and HIP(t−1). A location $VP_t$ of the initial virtual proxy point is computed as the intersecting point of the line segment (L) and the polygonal surface objects.

Figure 14:
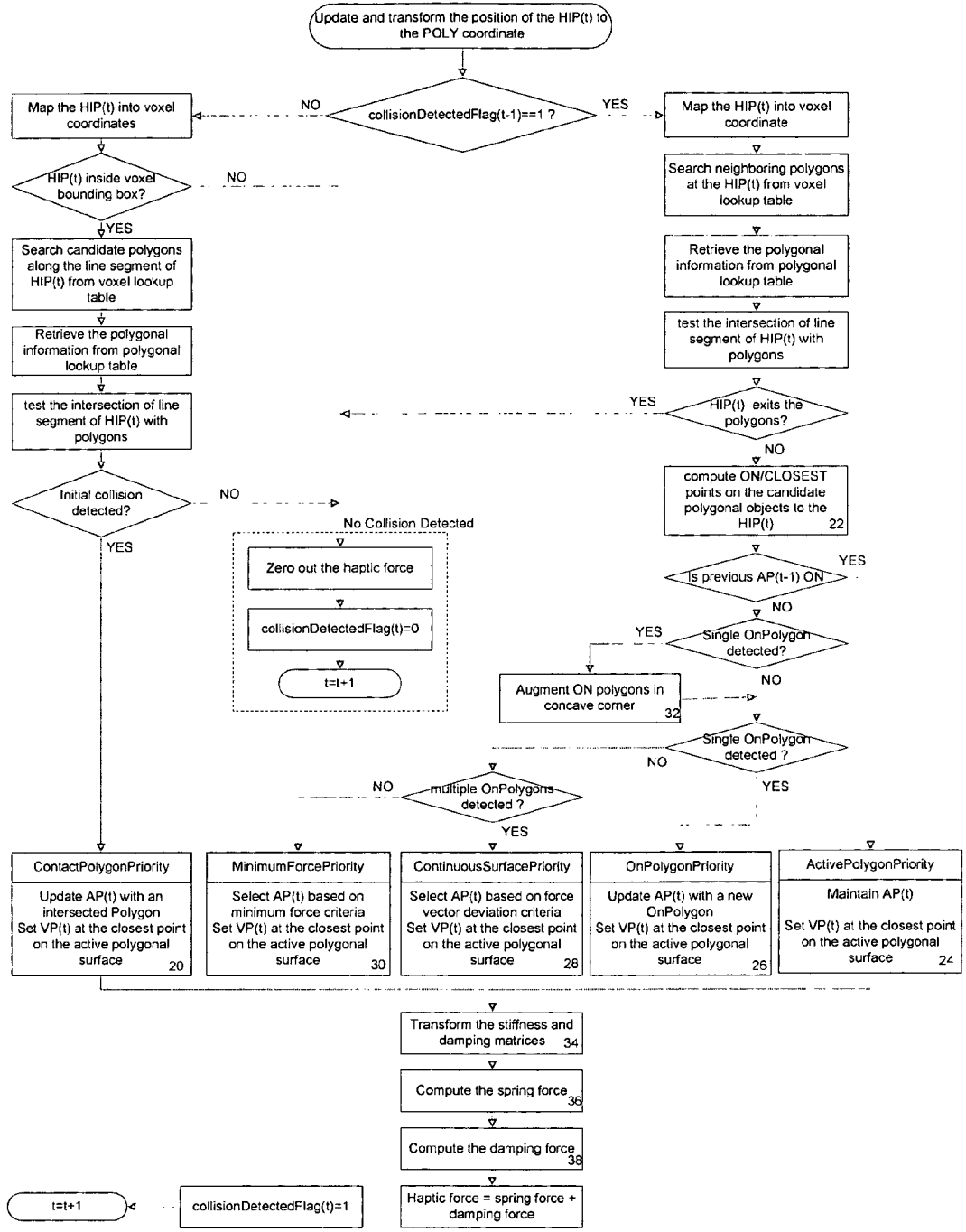
FIG. 14 is a flow diagram of an embodiment of a haptic rendering algorithm according to the present invention.

FIG. 14 shows a flowchart detailing an embodiment of a haptic rendering algorithm (block 2508 of FIG. 2) based on polygonal surface objects according to the present invention. In step S100, the position of HIP(t) is updated and transformed to the polygon reference frame. In step S101, the algorithm determines whether collisionDetectedFlag(t−1) has a value of 1, that is, whether a collision has been detected. If the collisionDetectedFlag is not set, meaning no collision has been detected at (t−1), in step S103, the algorithm maps the HIP(t) into voxel coordinates. In step S105, the algorithm determines whether the HIP(t) is inside a voxel bounding box. If not, no collision is presently detected, and the algorithm proceeds to step S115 where the haptic force felt by the user is set to zero, step S117 where collisionDetectedFlag(t) is set to zero, and step S119 where the time advances to t=t+1. If step S105 determines that the HIP(t) is inside a voxel bounding box, the algorithm proceeds to step S107 and searches candidate polygons along a line segment of HIP(t) from a voxel lookup table. In step S109, the algorithm retrieves polygonal information from a polygon lookup table. In step S111, the algorithm tests an intersection of the line segment of HIP(t) with the polygons and, in step S113, determines whether an initial collision is detected. If no collision is detected, the algorithm proceeds to steps S115, S117, and S119 as described above. If a collision is detected, the algorithm proceeds to step S132 (described below).

In contrast, in step S101, if collisionDetectedFlag(t−1) has a value of 1, the algorithm follows the right branch of the flowchart. In step S102, the algorithm maps HIP(t) into voxel coordinates. In step S104, the algorithm searches neighboring polygons at the HIP(t) from a voxel lookup table. In step S106, the algorithm retrieves polygonal information from a polygon lookup table. In step S108, each neighboring polygon is tested to determine whether it is intersected by the line segment from HIP(t−1) to HIP(t). In step S110, the algorithm uses this information to determine whether the HIP(t) has exited the polygons. If so, the HIP is no longer penetrating the haptic object, and the algorithm proceeds to steps S115, S117, and S119 as described above.

Figure 15:
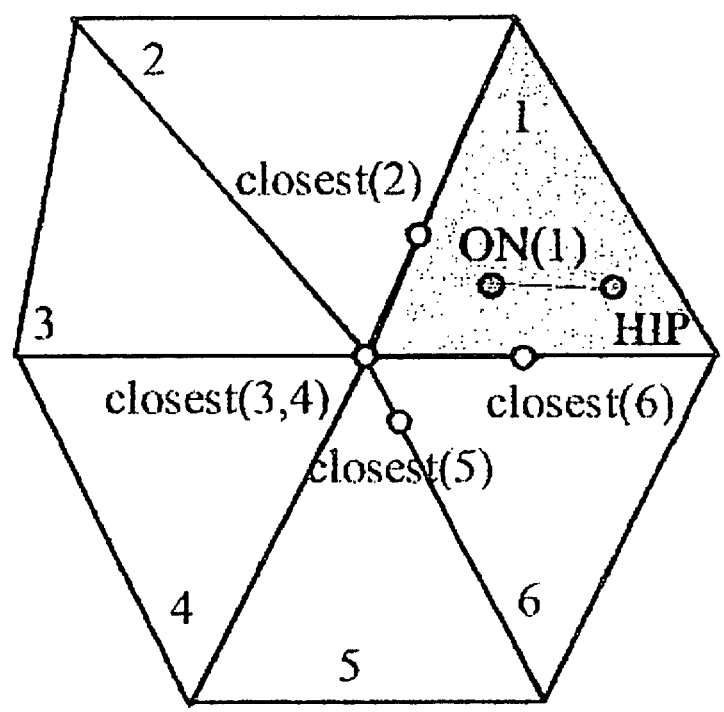
FIG. 15 is a pictorial representation of multiple polygons with HIP projection.

If step S110 determines that the HIP has not exited the polygons, the algorithm proceeds to step S112 where the algorithm projects the HIP(t) on each neighboring polygon along the corresponding surface normal vectors of the polygons. Referring to FIG. 15, if the projected HIP(t) is within a polygon, the algorithm sets the polygon as an On-Polygon and stores the intersecting point. Otherwise, the algorithm finds a point on a boundary of the polygon that is closest to the projected HIP(t) (all within the plane of the polygon) and stores the point. This process is repeated for each neighboring polygon. The algorithm then has decision points based on whether an Active Polygon from the previous time cycle, AP(t−1), was set to be an On-Polygon in step 22 and whether only a single polygon was set to be an On-Polygon in the current cycle. Each case is handled as described below.

In step S114, the algorithm determines whether a previous active polygon (on which the virtual proxy point was in contact) is still an On-Polygon. If so, in step S124 (ActivePolygonPriority), this polygonal surface has priority to be the active polygon, even if other polygons are identified as On-Polygons. AP(t) is therefore maintained, and VP(t), the virtual proxy point, is set at the closest point on the active polygonal surface. This virtual proxy point (VP(t) at time (t) is determined by drawing a normal to the nearest active polygonal surface from the HIP(t).

Figure 15A:
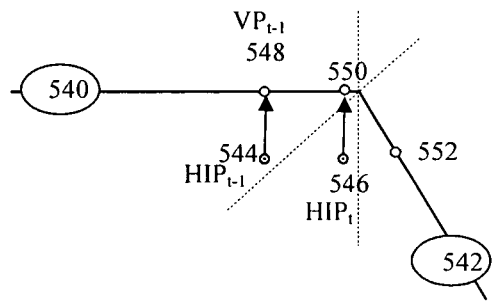
FIG. 15a is a pictorial representation of an active polygon priority behavior.

For example, FIG. 15a shows a convex portion of a virtual object defined by two adjoining surfaces 540 and 542. When the HIP at t−1 was at a location 544, the surface 540 is On-Polygon and 542 is not On-Polygon. The virtual proxy point location at (t−1) lies at a location 548. If the HIP moves to a location 546, both of the surfaces 540 and 542 are On-Polygons and locations 550 and 552 are candidates for proxy point location. In this situation, the surface 540 will be selected as an active polygon and the proxy point location will be updated at the location 550. Granting the previous active polygon priority in this way prevents the choice of the location 552 for the proxy point, which would result in an unnatural jump in the proxy point position and the resulting haptic interaction forces experienced by the user. That is, as the HIP moves from its location at HIP(t−1) 544 to HIP(t) 546 the forces felt by the user should be perpendicular to the surface 540 and not change direction discontinuously to become perpendicular to surface 542.

If step S114 determines that the previous active polygon is not an On-Polygon, the algorithm proceeds to step S1116 to determine whether a single On-Polygon is detected. If a single On-Polygon is not detected in step S116, the algorithm checks again in step S1120. If a single On-Polygon is detected in step S116, the algorithm proceeds to step S118 and augments the On-Polygons for a concave corner before checking again for a single On-Polygon in step S120. If a single On-Polygon is detected in step S120, the algorithm proceeds to step S126 to update the Active Polygon with a new polygon as described below. If a single On-Polygon is not detected in step S120, the algorithm proceeds to step S122 and determines whether multiple On-Polygons are detected. If multiple On-Polygons are detected, the algorithm proceeds to step S128 to select an Active Polygon based on force vector deviation criteria as described below. Otherwise, the algorithm proceeds to step S130 to select a Active Polygon based on the minimum force criteria as described below.

Figure 16:
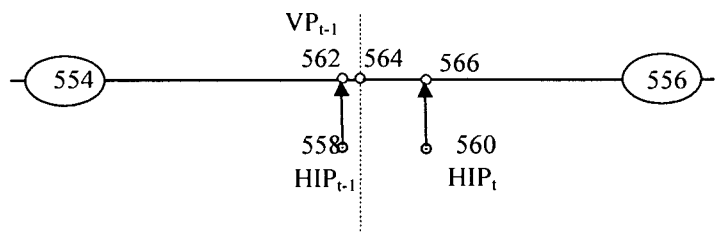
FIG. 16 is a pictorial representation of an On-Polygon priority behavior.

In step S126 (OnPolygonPriority), AP(t) is updated with a new On-Polygon and VP(t) is set at the closest point on the active polygonal surface. For example, as shown in FIG. 16, a virtual object has two adjoining surfaces 554 and 556. At a time (t−1), the HIP is at a location 558 and the proxy point is at a location 562. When the HIP crosses over a surface border line 564 as the HIP moves from the location 558 to a location 560, a surface 556 becomes On-Polygon and a location 566 becomes the new proxy point location. Thus, if a new single On-Polygon is detected, then the new single On-Polygon becomes the active polygon.

Figure 17:
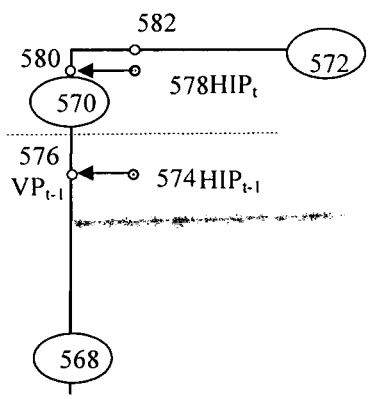
FIG. 17 is a pictorial representation of a continuous surface priority behavior.

In step S128 (ContinuousSurfacePriority), AP(t) is selected based on force vector deviation criteria and VP(t) is set at the closest point on the active polygonal surface. The algorithm detects the multiple new On-Polygons as illustrated in FIG. 17, which shows a convex portion of a virtual object defined by three surfaces, 568, 570, and 572. As the HIP moves from a location 574 to a location 578, the algorithm detects two new On-Polygon surfaces, 570 and 572. Thus, locations 580 and 582 are candidates for a new virtual proxy point location. In this situation, the algorithm computes possible candidates of force vector, excluding a damping component, and compares a force vector deviation from a previous force vector deviation. The algorithm determines the active polygon so as to minimize the following objective function:

$$J_{continuousSurface} = \min_{i} \|f_{si,t} \cdot f_{t-1}\|$$

where $f_{si,t}$ represents a unit vector of a spring force vector defined by a current location of the HIP and a possible location of the virtual proxy point on the ith polygon and $f_{t-1}$ represents a unit vector of a haptic force displayed at previous time. In one embodiment, the surface 570 will be the new active polygon and a location 580 will be the new proxy point position.

Figure 18:
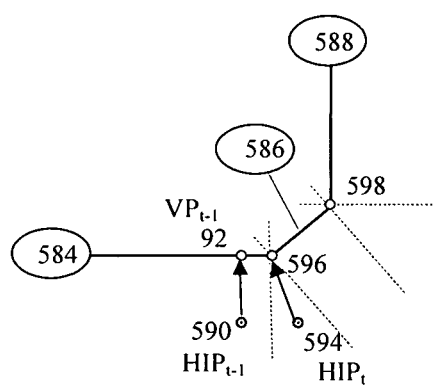
FIG. 18 is a pictorial representation of a minimum force priority behavior.

In step S130 (MinimumForcePriority), AP(t) is based on minimum force criteria and VP(t) is set at the closest point on the active polygonal surface. As shown in FIG. 18, the HIP lies at position where no On-Polygon can be detected. FIG. 18, illustrates a concave portion of a virtual object defined by three surfaces, 584, 586, and 588. When the HIP moves from a location 590 to a location 594, no surface is On-Polygon. A location 596 is the closest point to the surfaces 586 and 584, a location 598 is the closest point to the surface 588. In this situation, the algorithm computes distances between the current HIP and possible proxy point locations and determines a virtual proxy location to minimize the following objective function:

$$J_{minimumSpringForce} = \min_{i} \|x_{hip} - x_{i,vp}\|$$

where $x_{i,vp}$ represents a position of the possible virtual proxy point on the ith polygon and $x_{hip}$ represents a position of the current haptic interface point. In this situation, the algorithm sets either the surface 584 or the surface 586 as the On-Polygon depending on their processing sequence and the location 596 will be the proxy point location.

In step S132 (ContactPolygonPriority), AP(t) is updated with an intersected polygon and VP(t) is set at the closest point on the active polygonal surface. The algorithm augments the On-Polygon objects when a haptic interface point lies in a concave corner where the algorithm detects one On-Polygonal object and multiple concave surfaces. In this situation, the application sets the concave polygonal surface to On-Polygon so that continuous haptic rendering can happen at the concave corner. FIGS. 19 and 20 show a portion of a concave corner represented by three surfaces, 500, 502, and 504. FIG. 19 is the x-y view of the corner and FIG. 20 is the y-z view of the corner. As the haptic interface point moves from a location 506 (with a proxy point location 508) to a location 510 (FIG. 20), which is into or out of the page in FIG. 19, the surface 504 becomes the only On-Polygonal object. In order to avoid the situation in which the algorithm sets the surface 504 as an active polygonal surface due to On-Polygon priority behavior and selects a location 514 as the proxy point location, the algorithm augments the two concave surfaces 500 and 502 into On-Polygon objects. As a result, a location 512 will be a proxy point location according to continuous surface priority behavior.

In step S134, stiffness and damping matrices defined in tool coordinates as constant parameters are transformed into an inertial coordinate frame. When the physical haptic system 30 has different transmission devices, such as a cable driven transmission and a direct-driven transmission, isotropic spatial stiffness and damping gains can cause instability because the physical system has different dynamic properties in different directions. For this reason, the spatial stiffness and damping matrices which may be defined with respect to the tool coordinates, need to be transformed into the inertial coordinate frame. The algorithm computes an adjoint transformation matrix based on current rotational and translational matrices and transforms the spatial stiffness and damping matrices. Let $^{T}K_{S}$ and $^{I}K_{S}$ denote the stiffness matrices measured in tool frame and inertial frame, respectively. Let $Ad_{g}$ denote the adjoint transformation matrix given as $$Ad_g = \begin{bmatrix} R & \hat{p}R \\ 0 & R \end{bmatrix}$$

Given a vector $p=(px, py, pZ)^T$, $\hat{p}$ denotes a skew-symmetric matrix used for representing a cross product as a matrix-vector product:

$$\hat{p} = \begin{pmatrix} 0 & -p_x & p_y \\ p_x & 0 & -p_z \\ -p_y & p_z & 0 \end{pmatrix}$$

where R is the rotational matrix and p is the translational vector.

The algorithm computes the stiffness matrix in the inertial frame:

$$^{I}K_S = Ad_g^{TT} {}^T K_S Ad_g$$

In step S136, the algorithm computes a spring haptic force vector based on the location of the haptic interface point and the virtual proxy point location according to Hooke's law:

$$F_{spring}(t) = {}^{I}K_S(x_{vp} - x_{hip})$$

where $x_{vp}$ represents a position of a current virtual proxy point, and $x_{hip}$ represents a position of a current haptic interface point.

In step S138, the algorithm computes a damping haptic force vector based on the relative motion between the haptic interface point and the virtual proxy point:

$$F_{damping}(t) = {}^{I}K_D(\dot{x}_{vp} - \dot{x}_{hip})$$

where $\dot{x}_{vp}$ represents the velocity of the virtual proxy point, $\dot{x}_{hip}$ represents the velocity of the haptic interface point, and $^{I}K_D$ represents the spatial damping matrix in an inertial frame.

In step S140, the sum of the damping force and spring force is sent to the physical haptic device 30 as a desired force output (step S718 of FIG. 5). Prior to controlling the actuators (block 2512 of FIG. 2) of the haptic device 30 to output force feedback, the force mapping process (block 2510 of FIG. 2) converts the desired force, $F_{desired}$, to joint torque, $\tau$:

$$\tau = J^T F_{desired}$$

where $J^T$ is a Jacobian transpose. The computing system 20 then controls the actuators of the haptic device 30 to output the joint torque, $\tau$.

In step S142, collisionDetectedFlag(t) is set to 1. In step S144, the time (t) advances to (t+1).

In cases where there may be a transmission with compliance, backlash, hysteresis, or nonlinearities between the haptic device drive (e.g., motors) and position outputs (e.g., joints), it is beneficial to include position sensors on both the drive end and load end of the transmission. The load end sensors are used to compute all joint and endpoint positions because they will most accurately reflect the actual values. The drive end sensors are used to compute velocities in any damping computations, such as for Fdamping above, which helps avoid exciting the transmission dynamics.

According to one embodiment, the desired force feedback (or output wrench) of the haptic device 30 is determined based on a proximity of a portion of the haptic device 30 (e.g., the tool 50) to a virtual (or haptic) boundary associated with the representation of the anatomy. Thus, if the tool 50 is disposed a sufficient distance from the haptic boundary, a controller commands no haptic forces, and the user is free to move the tool 50 as if exploring empty space.

However, as the tool 50 approaches or contacts the haptic boundary, the controller commands torques to the motors so as to exert the appropriate wrench on the user's hand. Preferably, a magnitude of the force feedback increases as the tool 50 approaches the virtual boundary and does not present a discontinuous step that may induce oscillation or unwanted vibration. For example, as the tool 50 approaches the haptic boundary, the haptic device 30 may exert a force in a direction opposite a direction of movement of the tool 50 by the user such that the user perceives a repulsive or counteracting force that slows and/or stops movement of the tool 50. In one embodiment, a rate of increase of the force as the tool 50 continues moving toward the haptic boundary may be, for example, in a range of 5 N/mm to 50 N/mm. In another embodiment, the rate of increase of the force may be approximately 20 N/mm. In this manner, the user is constrained to not penetrate the haptic boundary too deeply.

When the tool 50 contacts the haptic boundary, the force may be such that the user feels as if the tool 50 has collided with a physical object, such as a wall. The magnitude of the force may prevent the user from penetrating the haptic boundary (e.g., a magnitude of approximately 100 N or greater) but is preferably set so that the user may breach the haptic boundary if desired (e.g., a magnitude in a range of approximately 20 N to approximately 60 N). Thus, the computing system 20 may be programmed to permit the user to overcome the force feedback and move the haptic device 30 to a desired location. In this manner, the haptic device 30 constrains the user against inadvertently violating the haptic boundary, but the user has the option to overpower the haptic device 30 and thus retains full control over the surgical procedure.

In one embodiment, the surgical system 10 includes a haptic tuning feature for customizing a force feedback function of the haptic object for a particular user. Such a feature is advantageous because each user has a unique surgical technique. Thus, different users may use differing amounts of force when maneuvering the tool 50. For example, users who maneuver the tool 50 with a light touch may sense haptic feedback earlier than users with a heavier touch. Rather than requiring the user with the heavier touch to alter his surgical technique to sufficiently sense the haptic feedback, the haptic tuning feature enables the force feedback function to be adjusted to accommodate each particular user. By adjusting (or tuning) the force feedback function, the user can manipulate the tool 50 with his preferred degree of force and still sufficiently perceive the haptic feedback exerted by the haptic device 30. As a result, the user's ability to maintain the tool within the haptic boundary is improved. For example, a force feedback curve includes a function F(d) that relates force F to distance d. The function F(d), for example, may result from or be a product of the haptic object, a coupling stiffness, or a stiffness function. In one embodiment, $F_i$ is a typical haptic interaction force for a user (or a group of users), and $d_i$ is a penetration depth or distance (e.g., penetration of the tool 50 into the haptic object) where $F_i=F(d_i)$ is true. Shifting or offsetting the function F(d) to the left by, for example, $d_i$, results in a force feedback function $F(d+d_i)$ that causes the force F to be applied earlier (i.e., beginning at a penetration distance of $-d_i$ rather than at a penetration distance of zero) in a tool's approach to a haptic boundary. Similarly, shifting or offsetting the function F(d) to the right causes the force F to be applied later in the tool's approach to the haptic boundary.

Thus, for a user with a surgical technique that is forceful, it is advantageous to offset the function F(d) to the left to prevent the user from inadvertently pushing too far into the haptic boundary. Thus, haptic tuning may be accomplished by offsetting a force feedback curve for controlling the haptic device 30 by a desired value. Haptic tuning can also be accomplished by altering a size of a haptic object. For example, a size of a repulsive haptic object can be increased resulting in a haptic object. Similarly, a size of a representation of a surgical tool coupled to the haptic device 30 may be altered. For example, a size of a radius of a tip of a virtual tool that interacts with a haptic object can be increased resulting in a virtual tool. For a haptic object that acts as a container, tuning can be accomplished, for example, by reducing a size of the haptic object.

Figure 21:
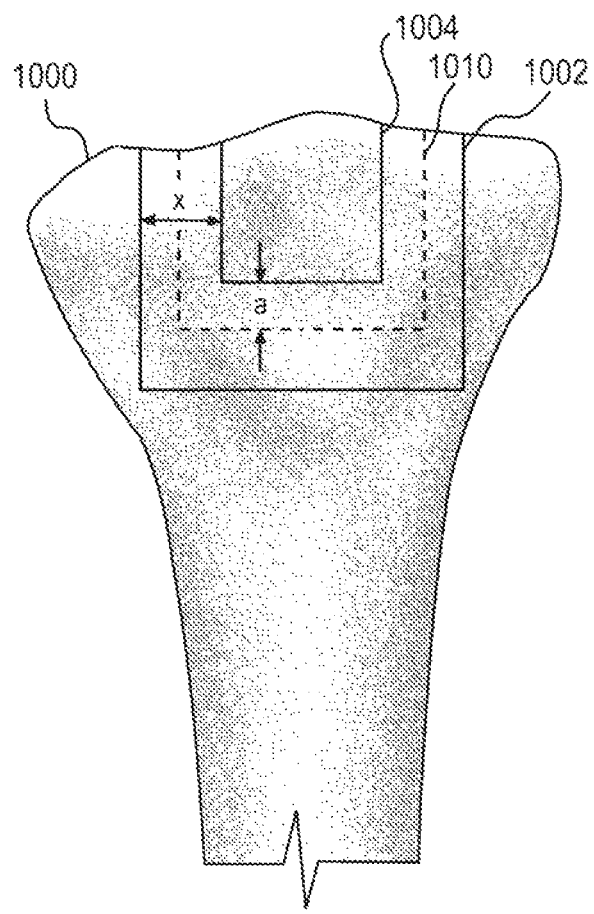
FIG. 21 is a diagram of an embodiment of a dual proxy haptic rendering applied to a bone.

Referring to FIG. 21, a bone 1000 is to have a region removed to permit an implant to be cemented in the cavity formed by the bone removal. This cavity is defined by an ideal expected cutting surface 1002 so that the haptic interface generates the appropriate forces as the user removes bone material from the bone 1000. A second surface, termed a primary proxy surface 1004, is defined at a predetermined constant distance (x) from the expected cutting surface 1002.

Between the expected cutting surface 1002 and the primary proxy surface 1004 is defined a third surface, termed the secondary proxy surface 1010. This secondary proxy surface 1010 is positioned between the expected cutting surface 1002 and the primary proxy surface 1004, at a desired offset distance (a) from the primary proxy surface 1004.

Figure 21A:
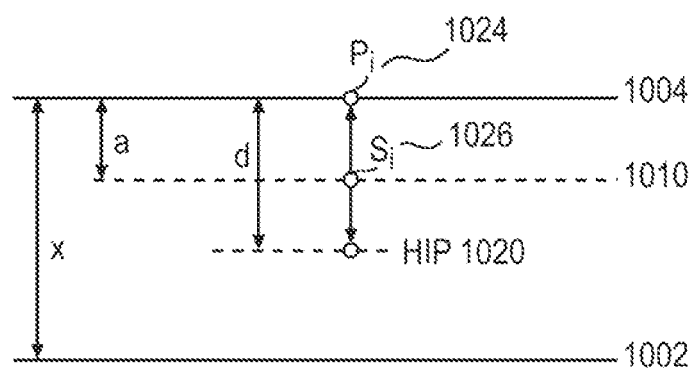
FIG. 21a is a diagram of the force vector on a HIP.

Referring also to FIGS. 21 and 21*a*, the location within this haptic representation at which the force on the point being generated is the HIP 1020. The position on the primary proxy surface 1004 which corresponds to the position of the HIP 1020 projected perpendicularly onto the primary proxy surface 1004 is termed the primary proxy $P_i$ 1024. The position on the secondary proxy surface 1010 which corresponds to the position of the HIP 1020 projected perpendicularly onto the secondary proxy surface 1010 is termed the secondary proxy $S_i$ 1026.

The force applied at the HIP 1020 is determined, in part, by the location of the HIP 1020 relative to the secondary proxy 1026 in the haptic space. If the penetration depth (d) is less than the desired offset distance (a), then the force is directed toward the primary proxy 1024 and is a first function of the distance between the HIP 1020 and the primary proxy 1024. In one embodiment, the force is a constant value, for example 0.

As bone is removed and the HIP 1020 moves toward the expected cutting surface 1002, the HIP 1020 reaches the location of the secondary proxy surface 1010. At this location, a new force is calculated to replace the original force. This new force is directed toward the secondary proxy 1026 and has a magnitude determined in part by the distance between the HIP 1020 and the secondary proxy 1026. In one embodiment, the force is linearly proportional to the distance between the secondary proxy and the HIP.

Thus, the surgeon can remove bone without feeling a resistive force until a predetermined depth into the bone is reached. At this point, a resistive force is generated that gets larger and larger as the tool approaches the expected cutting surface. The steps of the algorithm then become, define the offset (a) and compute the penetration depth (d) as the absolute magnitude between the HIP 1020 and the primary proxy 1024 at the present time.

$$d=\|(P_i-HIP)\|$$

Next the unit force vector û is determined from the expression:

$$\hat{u}=(P_i-HIP/\|(P_i-HIP)\|$$

The secondary proxy ($S_i$) is then defined by the primary proxy ($P_i$), the unit force vector (û), and the offset (a):

$$S_i=Pi-\hat{u}\cdot a$$

The spring force applied is determined, in part, by the spring constant ($K_p$) according to the expression:

$F=a$ constant e.g. 0 if $d<a$ and $K_p(Si-HIP)$ otherwise.

To enable each user to tune the force feedback function, the computing system 20 preferably includes programming to enable a graphical selection interface that can be displayed on the display device 23. For example, the graphical selection interface may be a graphical interface that enables the user to set a tuning value, for example, between 0.0 and 1.0 and/or a graphical interface that enables the user to select, for example, tuning for a "Light," "Medium," or "Heavy" touch. The computing system 20 may also be programmed to store a desired value of a tuning setting and to associate the desired value with a particular user (e.g., using a user ID tied to a user preference data file) so that the user does not have to select the tuning setting prior to each use of the surgical system 10.

Referring again to FIG. 1, a typical haptic robot as shown includes a number of joints and drives all designed to move an end effecter to any point in space and provide tactile feedback to the user. The robot of FIG. 1 has multiple degrees of freedom, including rotation of the base, shoulder joint, elbow joint and wrist joint. Each of the joints is driven by a transmission, which in various embodiments include two cables directed over pulleys or direct drive motors. The force on/at a point in Cartesian haptic space is given by $$F_{cartesian}=f(x_{hip},x_{proxy},K_p,\dot{x}_{hip},\dot{x}_{proxy},K_d)$$

Where: $x_{hip}$ is the haptic interaction point; $x_{proxy}$ is the location on the surface corresponding to the HIP location; Kp is the restoring spring force constant; $\dot{x}_{hip}$ is the velocity of the haptic interaction point; $\dot{x}_{proxy}$ is the velocity of the proxy; and Kd is the damping force constant. The torque on a joint necessary to bring a joint to, or maintain a joint, at a position can be calculated by applying the Jacobian Transpose to the force necessary to move the location in Cartesian space:

$$\tau_{joint}=J^TF_{cartesian}$$

The stability of the haptic feedback, that is, the avoidance of oscillation at the intended position in one embodiment is given by the function:

haptic stability=$f(\alpha_1,\alpha_2,\alpha_3,\alpha_4)$ where $\alpha_1$ is a function of the sampling time (for example 1 $KH_z$); $\alpha_2$ is a function of the sensor resolution; $\alpha_3$ is a function of the spring constant Kp and the damping constant Kd for the transmission; and $\alpha_4$ is a function of the physical damping (for example, friction).

The damping force (Fd) which is to be applied to the HIP is given by the equations:

$$Fd=Kd(dx/dt_{HIP}-dx/dt_{proxy})$$

where $dx/dt=Jd\theta_c/dt$ and $d\theta/dt=[d\theta_{1c}/dt,d\theta_{2c}/dt,d\theta_{3c}/dt,d\theta_{4c}/dt,d\theta_{5d}/dt]^T$ where $d\theta_c/dt$ is the joint velocity of a cable driven joint and $d\theta_d/dt$ is the velocity of a direct driven joint. A cable driven joint has transmission compliance. The transmission compliance between the joint and the motor introduces a greater phase-delay in joint velocity computation than a direct driven joint. In a mixed drive system, one with both direct and transmission drives, it is beneficial to implement the damping action in joint space so that the direct-driven joint will not be affected by the phase-delay of the joint velocity computation from any cable driven joints. There are two approaches to doing this, the joint-space spring and damping force method or the Cartesian-space force and Joint-space damping method.

In the Joint-space spring and damping method: first the joint angles of the HIP and the proxy are defined by:

$\theta_{proxy}$=inverse kinematic($p_i$) and $\theta_{HIP}$=inverse kinematic($h_i$)

where p and h are the proxy positions and HIP positions respectively.

In one embodiment, the joint space stiffness and damping coefficients are then obtained from the diagonals of the Jacobian of θ by the equation:

$$K_{pj}\approx J^T(\theta)K_{px}J(\theta)$$

$$K_{dj}\approx J^T(\theta)K_{dx}J(\theta)$$

In other embodiments, the joint space stiffness $K_{pj}$ and the damping coefficient $K_{dj}$ are obtained in other ways, such as setting predetermined fixed values, scheduling, etc.

Finally, the torque is calculated from the angles and the angular velocity:

$$\tau=K_{pj}(\theta_{proxy}-\theta_{HIP})-K_{dj}d\theta/dt$$

In the Cartesian-space spring and joint-space damping method, the Cartesian spring force is defined by:

$$F_{spring}=K_{px}(p_i-h_i)$$

where $K_{px}$ is the Cartesian spring force constant and ($p_i-h_i$) is the distance between the location of the proxy point (p) and the location of the HIP (h). The corresponding joint torque ($\tau_{spring}$) equivalent to the spring force is then:

$$\tau_{spring}=J^TF_{spring}$$

In one embodiment, the damping torque ($\tau_{damping}$) is next calculated. When a user moves along the surface, the joint space damping algorithm causes a dragging force. In order to eliminate this frictional force along the surface, the following procedure is performed:

First, a wrench vector $F_6$, which is a force/moment pair, is formed:

$$F_6 = \begin{bmatrix} F \\ M \end{bmatrix}$$

where $F_6$ is the generalized force(wrench) vector $F_6 \in R^6$, and $F \in R^3$ represents the Cartesian force vector and $F \in R^3$ represents the Cartesian moment vector.

Next, the wrench direction vector, $$u = \frac{F_6}{\|F_6\|}$$

is computed.

The wrench direction vector is mapped into the corresponding joint space vector:

$$v = J^T(\theta) u$$

The weighting factor, $$w = \frac{|v|}{|v|_\infty},$$
$$|v|_\infty = \max\{|v_i|\},$$
$$i = 1, \dots, n$$

is then computed and
so is the damping force, according to the equation:

$$\tau_{damping} = \begin{bmatrix} w_1 & 0 & 0 & 0 & 0 & 0 \\ 0 & w_2 & 0 & 0 & 0 & 0 \\ 0 & 0 & w_3 & 0 & 0 & 0 \\ 0 & 0 & 0 & w_4 & 0 & 0 \\ 0 & 0 & 0 & 0 & w_5 & 0 \\ 0 & 0 & 0 & 0 & 0 & w_6 \end{bmatrix} \cdot \begin{bmatrix} K_{dj_1} & 0 & 0 & 0 & 0 & 0 \\ 0 & K_{dj_2} & 0 & 0 & 0 & 0 \\ 0 & 0 & K_{dj_3} & 0 & 0 & 0 \\ 0 & 0 & 0 & K_{dj_4} & 0 & 0 \\ 0 & 0 & 0 & 0 & K_{dj_5} & 0 \\ 0 & 0 & 0 & 0 & 0 & K_{dj_6} \end{bmatrix} \cdot \begin{bmatrix} \dot{\theta}_1 \\ \dot{\theta}_2 \\ \dot{\theta}_3 \\ \dot{\theta}_4 \\ \dot{\theta}_5 \\ \dot{\theta}_6 \end{bmatrix}.$$

Finally the two joint torques are combined:

$$\tau = (\tau_{damping}) + (\tau_{spring})$$

The foregoing description of the various embodiments of the invention is provided to enable any person skilled in the art to make and use the invention and its embodiments. Various modifications to these embodiments are possible, and the generic principles presented herein may be applied to other embodiments as well.

While the invention has been described in terms of certain exemplary preferred embodiments, it will be readily understood and appreciated by one of ordinary skill in the art that it is not so limited and that many additions, deletions and modifications to the preferred embodiments may be made within the scope of the invention as hereinafter claimed. Accordingly, the scope of the invention is limited only by the scope of the appended claims.

What is claimed is:

1. A method for generating a haptic force comprising the steps of:
   defining a haptic interaction point (HIP) position in virtual space, the HIP position corresponding to a physical point associated with a surgical tool;
   defining a primary proxy position on a primary proxy surface;
   defining a secondary proxy position on a secondary proxy surface, wherein the secondary proxy surface is positioned at a predetermined distance from the primary proxy surface and between the primary proxy surface and an expected cutting surface of a bone;
   generating a first haptic force, by a haptic device, based on the primary proxy position and the HIP position when the HIP position is located between the primary proxy surface and the secondary proxy surface at a distance less than or equal to the predetermined distance from the primary proxy position, wherein the first haptic force is directed toward the primary proxy position; and
   generating a second haptic force, by a haptic device, based on the secondary proxy position and the HIP position when the HIP position is located between the secondary proxy surface and the expected cutting surface at a distance greater than the predetermined distance from the primary proxy position, wherein the second haptic force is directed toward the secondary proxy position.

2. The method of claim 1 wherein the predetermined distance is a desired offset distance.

3. The method of claim 1 wherein the second haptic force is a function of a distance between the secondary proxy position and the HIP position.

4. The method of claim 1 wherein the first haptic force is determined based, at least in part, on a distance between the primary proxy position and the HIP position.

5. The method of claim 1 wherein the secondary proxy position is determined based, at least in part, on interactions between the HIP and a virtual haptic object.

6. The method of claim 1 wherein the first haptic force is a non-zero constant value.

7. The method of claim 1 wherein the second haptic force is linearly proportional to the distance between the secondary proxy and a virtual haptic object.

8. The method of claim 7 wherein the virtual haptic object corresponds to the expected cutting surface of the bone.

9. The method of claim 1 wherein the first and second haptic forces are each non-zero.

10. An apparatus for generating a haptic force on a user comprising:
    a computer system comprising a processor configured to execute a series of steps to determine and generate the haptic force, the steps comprising:
    defining a haptic interaction point (HIP) position in virtual space, the HIP position corresponding to a physical point associated with a surgical tool;
    defining a primary proxy position on a primary proxy surface;
    defining a secondary proxy position on a secondary proxy surface, wherein the secondary proxy surface is positioned at a predetermined distance from the primary proxy surface and between the primary proxy surface and an expected cutting surface of a bone;
    generating a first haptic force, by a haptic device, based on the primary proxy position and the HIP position when the HIP position is located between the primary proxy surface and the secondary proxy surface at a distance less than or equal to the predetermined distance from the primary proxy position, wherein the first haptic force is directed toward the primary proxy position; and
    generating a second haptic force, by a haptic device, based on the secondary proxy position and the HIP position when the HIP position is located between the secondary proxy surface and the expected cutting surface at a distance greater than the predetermined distance from the primary proxy position, wherein the second haptic force is directed toward the secondary proxy position.

11. The apparatus of claim 10 wherein the second haptic force is determined, at least in part, in response to a distance between the secondary proxy position and the HIP position.

12. The apparatus of claim 10 wherein the first haptic force is determined based, at least in part, on a distance between the primary proxy position and the HIP position.

13. The apparatus of claim 10 wherein the secondary proxy position is determined based, at least in part, on interactions between the HIP and a virtual haptic object.

14. The apparatus of claim 10 wherein the first haptic force is a non-zero constant value.

15. The apparatus of claim 10 wherein the second haptic force is linearly proportional to the distance between the secondary proxy and a virtual haptic object.

16. The apparatus of claim 15 wherein the virtual haptic object corresponds to the expected cutting surface of the bone.

17. The apparatus of claim 10 wherein the first and second haptic forces are each non-zero.

\* \* \* \* \*